(12) United States Patent
Park et al.

(10) Patent No.: US 6,271,278 B1
(45) Date of Patent: *Aug. 7, 2001

(54) HYDROGEL COMPOSITES AND SUPERPOROUS HYDROGEL COMPOSITES HAVING FAST SWELLING, HIGH MECHANICAL STRENGTH, AND SUPERABSORBENT PROPERTIES

(75) Inventors: Kinam Park, West Lafayette, IN (US); Jun Chen, Hatfield, PA (US); Haesun Park, West Lafayette, IN (US)

(73) Assignee: Purdue Research Foundation, West Lafayette, IN (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/855,499

(22) Filed: May 13, 1997

(51) Int. Cl.$^7$ ..................................................... C08F 36/04
(52) U.S. Cl. ..................... 521/150; 521/102; 521/109.1; 521/121; 521/125; 521/128; 521/130; 521/140; 521/142; 521/146; 521/149; 521/182; 521/183; 521/186; 521/187
(58) Field of Search .............................. 521/102, 109.1, 521/121, 125, 128, 130, 140, 142, 146, 149, 150, 182, 183, 186, 187

(56) References Cited

U.S. PATENT DOCUMENTS

| | | |
|---|---|---|
| 3,551,556 | 12/1970 | Kliment et al. . |
| 3,641,237 | 2/1972 | Gould et al. . |
| 3,826,678 | 7/1974 | Hoffman et al. . |
| 4,178,361 | 12/1979 | Cohen et al. . |
| 4,525,527 | 6/1985 | Takeda et al. . |
| 4,529,739 | 7/1985 | Scott et al. . |
| 4,649,164 | 3/1987 | Scott et al. . |
| 4,801,457 | 1/1989 | Heller et al. . |
| 5,002,814 | 3/1991 | Knack et al. . |
| 5,089,606 | 2/1992 | Cole et al. . |
| 5,147,343 | 9/1992 | Kellenberger . |
| 5,149,335 | 9/1992 | Kellenberger et al. . |
| 5,154,713 | 10/1992 | Lind . |
| 5,292,777 | 3/1994 | DesMarais et al. . |
| 5,324,561 | 6/1994 | Rezai et al. . |
| 5,338,766 | 8/1994 | Phan et al. . |
| 5,352,448 | 10/1994 | Bowerstock et al. . |
| 5,403,870 | 4/1995 | Gross . |
| 5,424,265 | * 6/1995 | Weinstein ............................ 502/400 |
| 5,451,613 | 9/1995 | Smith et al. . |
| 5,462,972 | * 10/1995 | Smith et al. ........................... 521/64 |
| 5,624,967 | * 4/1997 | Hitomi et al. ......................... 521/64 |
| 5,750,585 | 5/1998 | Park et al. . |

FOREIGN PATENT DOCUMENTS

WO 97/27 884 A1 8/1997 (WO) .

OTHER PUBLICATIONS

K. Park, "Enzyme–digestible swelling hydrogels as platforms for long–term oral drug delivery: synthesis and characterization", Biomaterials (Sep. 1988), pp. 435–441, vol. 9, Butterworth & Co.

C.J. Benning, Plastic Foams: the physics and chemistry of product performance and process technology. vol. 1, Polymer Engineering & Technology, (1969) Chptrs. 6, 7, 9, 10, 14. Wiley–Interscience.

F. Rodriguez, Principles of Polymer Systems. $2^{nd}$ ed. (1982) pp. 363–378, Hemisphere Publ. Corp.

Plastic Foams, Part II. K. Frisch and J. Saunders, ed. (1973) Chptrs. 12, 15, 17. Marcel Dekker, Inc.

F.A. Shutov, Integral/Structural Polymer Foams: Technology, Properties and Applications. (1986) Chptrs. 1, 21. Springer Verlag.

"Absorbent PVA Material Finds Medical Applications," Medical Product Mfg. News Hotline (Apr. 1, 1995).

Vichterle et al., Hydrophilic gels for biological use, *Nature*, 185: 117–118, 1960.

Shalaby et al., In vitro and in vivo studies of enzyme–digestible hydrogels for oral drug delivery, *J. Controlled. Rel.*, 19: 131–144, 1992A.

Shalaby et al., Use of ultrasound imaging and fluoroscopic imaging to study gastric retention of enzyme–digestible hydrogels, *Biomaterials*, 13:289–296, 1992B.

Chirila et al., Poly (2–hydroxyethyl methacrylate) sponges as implant materials: In vivo and in vitro evaluation of cellular invasion, *Biomaterials*, 14: 26–38, 1993.

Skelly et al., Novel macroporous hydrogel adsorbents for artificial liver support haemoperfusion systems, *Polymer*, 20: 1051–1052, 1979.

Oxley et al., Macroporous hydrogels for biomedical applications: Methodology and morphology, *Biomaterials*, 14: 26–38, 1993.

Barvic et al., Biologic properties and possible uses of polymer–like sponges, *J. Biomed. Mater. Res.*, 1: 313–323, 1967.

(List continued on next page.)

*Primary Examiner*—John M. Cooney, Jr.
(74) *Attorney, Agent, or Firm*—James H. Meadows

(57) ABSTRACT

A superporous hydrogel composite is formed by polymerizing one or more ethylenically-unsaturated monomers, and a multiolefinic crosslinking agent, in the presence of particles of a disintegrant and a blowing agent. The disintegrant, which rapidly absorbs water, serves to greatly increase the mechanical strength of the superporous hydrogel and significantly shorten the time required to absorb water and swell. Superporous hydrogel composites prepared by this method have an average pore size in the range of 10 $\mu$m to 3,000 $\mu$m. Preferred particles of disintegrant include natural and synthetic charged polymers, such as crosslinked sodium carboxymethylcellulose, crosslinked sodium starch glycolate, and crosslinked polyvinylpyrrolidone. The blowing agent is preferably a compound that releases gas bubbles upon acidification, such as $NaHCO_3$. Improved hydrogel composites formed without a blowing agent are also provided.

40 Claims, 5 Drawing Sheets

OTHER PUBLICATIONS de Groot et al., Use of porous biodegradable polymer implants in meniscus reconstruction. 1) Preparation of porus biodegradable polyurethanes for the reconstruction of meniscus lesions, *Colloid and Polymer Science*, 268: 1073–1081, 1990.

Park et al., Hydrogel foams: A new type of fast swelling hydrogels, The 20th Annual Meeting of the Society for Biomaterials, Abstract #158, 1994.

Park et al., Honey, I blew up the hydrogels!, Pro. Intern. Symp. Control. Rel. Bioact. Mater., 21: 21–22, 1994.

Kon et al., A poly (HEMA) sponge for restoration of articular cartilage defects., *Plast. Reconstruct. Surg.*, 67: 288–194, 1981.

Krauch et al., Polymerization on a crystalline matrix. (in German), *Natur. Wissenscheften*, 55: 539–540, 1968.

Badiger et al., Porogens in the preparation of microporous hydrogels based on poly (ethylene oxides), *Biomaterials*, 14: 1059–1063, 1993.

Haldon et al., Structure and permeability of porous films of poly (hydroxy ethyl methacrylate), *Br. Polym. J.*, 4: 491–501, 1972.

Dusek et al., Structure and properties of hydrophilic polymers and their gels. XI. Microsyneresis in swollen poly(ethylene glycol methacrylate) gels inducted by changes in temperatures, *Coll. Czech. Chem. Commun.*, 34: 136–157, 1969.

Young, A. T., Microcellular foams via phase separation, *J. Vac. sci. Technol.*, A4: 1126–1133, 1985.

Kabra et al., Synthesis of fast response, temperature–sensitive poly (n–isopropylacrylamide) gel, *Polymer Communications*, 32: 322–323, 1991.

Yan et al., Synthesis of macroporous hydrogels with rapid swelling and deswelling properties for delivery of macromolecules, *Polymer Communications*, 36: 887–889, 1995.

Wu et al., Synthesis and characterization of thermally reversible macroporous poly (N–isopropylacrylamide) hydrogels, *Journal of Polymer Science: Part A: Polymer Chemistry*, 30: 2121–2129, 1992.

Kabra et al., Rate–limiting steps for solvent sorption and desorption by microporous stimuli–sensitive absorbent gels, in *Superabsorbent Polymers*, American Chemical Society, Washington, DC, 1994, 76–86.

Hartley et al., The mechanism of polyurethane foam formation, in Advances in Polyurethane Technology, John Wiley and Sons Inc., New York, NY, 1968, 139.

Klempner et al., Polymeric Foams, Hanser Publishers, New York, 1991, Pages.

Gordon, A. H., Electrophoresis of proteins in polyacrylamide and starch gels, American Elsevier Publishing Company, Inc., New York, NY 1971, Pages.

Arshady, R., Albumin microspheres and microcapsules: methodology of manufacturing techniques, *Journal of Controlled Release*, 14: 111–131, 1990.

Tanaka et al., Kinetics of swelling of gels, *J. Chem. Phys.*, 70: 1214–1218, 1979.

Gehrke, S. H., Synthesis, ewuilibrium selling, kinetics permeability and applications of environmentally responsive gels, in Responsive Gels: Volume Transitions II, Springer–Verlag, New York, 1993, 81–144.

Shutov, F. A., Cellular structure and properties of foamed polymers, in *Polymeric Foams*, Hanser Publishers, New York, 1991, 34–35.

Holly et al., Water wettability of hydrogels, in Hydrogels for Medical and Related Applications, American Chemical Society, Washington, DC, 1976, 252–266.

Ratner, B. D., Hydrogel surfaces, in *Hydrogels in Medicine and Pharmacy*. Vol. I. Fundamentals, CRC Press, Inc., Boca Raton, FL, 1986, 85–94.

Kanig et al., The mechanisms of disintegrant action, *Pharmaceutical Technology*, Apr. 1984: 50–63.

Gissinger et al., A comparative evaluation of the properties of some tablet disintegrants, *Drug Development and Industrial Pharmacy*, 6: 511–536, 1980.

Anderson et al., Polymerized lyotropic liquid crystals as contact lens materials, *Physica A*, 176: 151–167, 1991.

\* cited by examiner

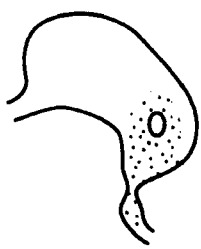
FIG. 5A
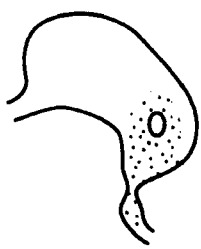
FIG. 5B
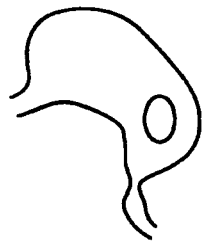
FIG. 5C
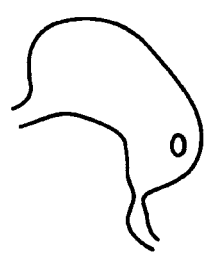
FIG. 5D
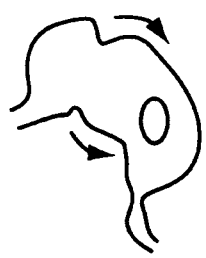
FIG. B-1
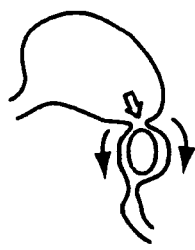
FIG. B-2
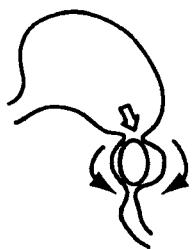
FIG. B-3
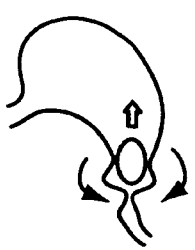
FIG. B-4
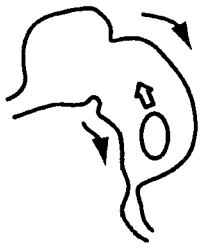
FIG. B-5

HYDROGEL COMPOSITES AND SUPERPOROUS HYDROGEL COMPOSITES HAVING FAST SWELLING, HIGH MECHANICAL STRENGTH, AND SUPERABSORBENT PROPERTIES

FIELD OF THE INVENTION

The present invention relates to swellable hydrogel compositions, and more particularly to porous compositions.

BACKGROUND OF THE INVENTION

A "hydrogel" is a crosslinked polymer network which is insoluble in water but swells to an equilibrium size in the presence of excess water. Research on hydrogels started in the 1960s with a landmark paper on poly(hydroxyethyl methacrylate) [Wichterle, O., et al., 1960]. Due to the unique properties of hydrogels and their potential applications in such areas as controlled drug delivery, various types of hydrogels have been synthesized and characterized. Most of this work has focused on lightly cross-linked, homogeneous homopolymers and copolymers.

The bulk polymerization, i.e., polymerization in the absence of added solvent, of monomers to make a homogeneous hydrogel produces a glassy, transparent polymer matrix which is very hard. When immersed in water, the glassy matrix swells to become soft and flexible. Although it permits the transfer of water and some low molecular weight solutes, such a swollen polymer matrix (hydrogel) is considered non-porous. The pores between polymer chains are in fact the only spaces available for the mass transfer, and the pore size is within the range of molecular dimensions (a few nanometers or less) [Chirila, T., et al., 1993]. In this case, the transfer of water or other solutes is achieved by a pure diffusional mechanism, which restricts the rate of absorption and to some extent the size of species that are absorbed [Skelly, P. J., 1979]. Homogeneous hydrogels have been used widely in various applications, especially in the controlled drug delivery area where limited diffusional characteristics are required [Oxley, H. R., 1993].

Porous hydrogels are usually prepared by a solution polymerization technique, which entails polymerizing monomers in a suitable solvent. The nature of a synthesized hydrogel, whether a compact gel or a loose polymer network, depends on the type of monomer, the amount of diluent in the monomer mixture, and the amount of crosslinking agent [Barvic, M. et al., 1967]. As the amount of diluent (usually water) in the monomer mixture increases, the pore size also increases up to the micron range [Chirila, T. et al., 1993]. Hydrogels with effective pore sizes in the 10–100 nm range and in the 100 nm–10 $\mu$m range are termed "microporous" and "macroporous" hydrogels, respectively. In practice, the terms "microporous" and "macroporous" are used interchangeably simply due to the fact that there is no unified definition of micro- and macro-pores in hydrogels. Accordingly, hydrogels having pores up to about 10 $\mu$m can be called either microporous or macroporous.

Porous hydrogels can be made by preparing hydrogels (usually from polymerizable monomers) in the presence of dispersed water-soluble porosigens, which can be removed later by washing with water to leave an interconnected meshwork (i.e., porous hydrogels) [Oxley, H. R. et al., 1993; Krauch, C. H. et al., 1968]. Examples of effective porosigens are micronized sucrose, lactose, and dextrin [Oxley, H. et al., 1993], sodium chloride [Kon, M. et al., 1981], and poly (ethylene oxides) (PEGs) [Badiger, M. et al., 1993].

Water itself can be used as a porosigen if a polymer network is formed in the frozen state. Monomers can be polymerized in the frozen state around aqueous crystals, and then water can be subsequently removed by thawing to result in a macroporous hydrogel [Oxley, H. R. et al., 1993; Haldon, R. A. et al., 1972]. In this approach, which is appropriately called a "freeze-thaw" technique, ice crystals function as the porosigen. When a polymer network is formed in an aqueous solution, the whole system can be freeze dried to sublimate ice crystals and leave a porous matrix [Loree, H. M. et al., 1989]. This "freeze-drying" technique is useful in the preparation of porous hydrogels from water-soluble polymers such as polysaccharides (e.g., sodium alginate) [Cole, S. M. et al., 1992]. To prepare porous hydrogels more effectively using the freeze-drying technique, salt can be added as another porosigen, and this increases the reproducibility of preparing porous materials [de Groot, J. H. et al., 1990].

Non-aqueous solutions can also be used as porosigens in polymerization of an oil-in-water emulsion system [Gross, J. R., 1995]. In this case, the water phase contains water-soluble monomers and a crosslinker and the oil phase is a volatile organic solvent. The continuous water phase is polymerized and this is followed by evaporation of the oil phase, which results in the porous structure.

The pore size of hydrogels prepared by the porosigen technique depends on the size of the porosigens. The introduction of a porosigen reduces mechanical strength significantly, although a negative effect on the mechanical properties can be minimized if the size of the porosigen is maintained below about 40 $\mu$m. In many cases where larger pores are necessary, microparticulate particles (e.g., sucrose crystals) in the range of 100–300 $\mu$m can be used [de Groot, J. H. et al., 1990]. The presence of such large sized pores will obviously make the porous hydrogels extremely weak.

In a solution polymerization, the monomers are usually mixed in a diluent which is good for both monomers and polymers. If, however, the diluent is a non-solvent for the polymer formed (e.g., PHEMA in water), the solubility of polymers dramatically decreases as the polymerization proceeds. This results in phase separation of the polymer-rich monomer phase into droplets, which then join together to form a network filled with large spaces (i.e., heterogeneous, porous hydrogels) by the end of the polymerization process. This process is called heterogeneous solution polymerization [Chirila, T. et al., 1993; Barvic, M. et al., 1967; Dusek, K. et al., 1969].

Phase separation can also be induced from the initially homogeneous polymer solution by altering the solvent quality. The solvent quality can be decreased by removing good solvent or adding non-solvent to a polymer solution or by changing the temperature. Many polymer solutions form a reversible gel upon changes in temperature. For example, gelatin in water becomes a gel when cooled below the critical miscibility temperature [Young, A. T., 1985]. In general, aqueous polymer solutions can be rapidly frozen to result in spinodal decomposition, and subsequent removal of water by freeze-dry sublimation yields porous hydrogels.

For polymers with a lower critical solution temperature (LCST), water becomes a non-solvent to the polymer and phase separation occurs as the temperature is increased above the LCST. This technique has been used to prepare porous hydrogels made of poly(N-isopropylpolyacrylamide) [Kabra, B. G. et al., 1991; Yan, Q. et al., 1995; Wu, X. S. et al., 1995], and crosslinked hydroxypropylcellulose [Kabra, B. G. et al., 1994]. The pore sizes of macroporous hydrogels prepared by phase separation are typically only a few micrometers. In addition, the overall porosity is very low and this implies that the pores are not well interconnected. The major limitation of the phase separation method is that only very limited types of porous hydrogels can be prepared. In addition, there is not much control over the porosity of the gels when prepared by phase separation.

Additionally, individual hydrogel particles can be surface crosslinked to form crosslinked aggregates of particles, thereby forming pores between the hydrogel particles. Such aggregate macrostructures are prepared by initially mixing the hydrogel particles (in the range of a few hundred micrometers) with a solution of a crosslinking agent, water, and hydrophilic organic solvent such as isopropanol [Rezai, E. et al., 1994]. Pores in such structures are present between hydrogel particles and the size of the pores is much smaller than the size of the particles. This approach is limited to absorbent particles having chemically active functional groups on the surface.

It is important to distinguish the microporous and macroporous structures of hydrogels with those of non-hydrogel porous materials, such as porous polyurethane foams. In the plastic foam area, micro- and macro-pores are indicated as having pores less than 50 $\mu$m and pores in the 100–300 $\mu$m range, respectively [de Groot, J. H. et al., 1990]. One of the reasons for this difference is that hydrogels with pores larger than 10 $\mu$m were rarely made, while porous plastics having pores in the 100–300 $\mu$m range are very common. Porous hydrogels with a pore size larger than 100 $\mu$m were made only recently [Park, H. et al., 1994A; Park, H. et al., 1994B], and that is probably why these definitions for porous hydrogels differ from those for porous plastics.

Microporous and macroporous hydrogels are sometimes called polymer "sponges" [Chirila, T. et al., 1993]. When a monomer, e.g., hydroxyethyl methacrylate (HEMA), is polymerized at an initial monomer concentration of 45 (w/w) % or higher in water, a hydrogel is produced with a porosity higher than the homogeneous hydrogels. These heterogeneous hydrogels are sometimes called "sponges" in the biomedical literature [Chirila, T. et al., 1993; Kon, M. et al., 1981]. The term "sponge" is not recommended, however, since it is better known as "rubber sponge" which is not a hydrogel in any sense. Moreover, the properties of rubber sponges are totally different from porous hydrogels. For example, rubber sponges release imbibed water upon squeezing, but porous hydrogels may not be squeezable—they may break into pieces with water entrapped in the polymer networks because of their hydrophilic nature.

U.S. Pat. No. 5,451,613 (issued to Smith et al.), and related patents, proposes making superabsorbent polymers by polymerizing a monomer solution containing carboxylic acid monomers and an effective amount of a crosslinking agent, in the presence of a carbonate blowing agent, to thereby form a microcellular hydrogel. The microcellular hydrogel is then chopped or ground and the pieces are used to form a core polymer. The core polymer is then surface crosslinked to provide superabsorbent particles.

U.S. Pat. No. 5,338,766 (issued to Phan et al.) proposes making a superabsorbent polymer foam from an unsaturated monomer having neutralized carboxyl groups reacted with an internal crosslinking agent. The monomer and crosslinking agent are expanded in the presence of a blowing agent and a solvent so as to form an expanded structure. The expansion and reaction are controlled to form the superabsorbent polymer material.

U.S. Pat. No. 5,154,713 (issued to Lind) proposes forming a superabsorbent polymer by forming a microcellular hydrogel from a (meth)acrylic acid monomer in the presence of a carbonate blowing agent. This material is then chopped into pieces and dried to produce a superabsorbent particulate polymer.

U.S. Pat. No. 4,525,527 (issued to Takeda et al.) proposes making a crosslinked acrylic resin having improved water absorbing properties. The acrylic resin is prepared by aqueous polymerization of acrylic acid, acrylamide, and a water soluble polyvinyl monomer.

One of the limiting factors of hydrogels has been the rather slow swelling property of dried hydrogels. For the dried hydrogels to swell, water has to be absorbed into the glassy matrix of the dried hydrogels. The swelling kinetics of the dried hydrogels thus depend on the absorption of water occurring by a diffusional process and the relaxation of the polymer chains in the rubbery region. Equilibrium swelling of dried hydrogels in an ordinary tablet size (e.g., 1 cm in diameter×0.5 cm height) usually takes at least several hours, and this may be too slow for many applications where fast swelling is essential. For example, hydrogels have been successfully used as a gastric retention device that can stay in the stomach of a dog for up to 60 hours [Shalaby, W. S. W. et al., 1992A; Shalaby, W. S. W. et al., 1992B]. In those studies, however, hydrogels had to be preswollen for a few hours before administering to the dog to avoid premature emptying into the intestine.

In an effort to overcome the slow swelling property of dried hydrogels, the present inventors have synthesized a superporous hydrogel that can swell within minutes regardless of the size of the matrix [Chen, J., 1997]. While these superporous hydrogels provided significantly fast swelling kinetics and high swelling extent, the mechanical strength of the fully swollen superporous hydrogels was too poor to be useful. In some cases, the fully swollen superporous hydrogels could not be picked up and broke easily due to their very poor mechanical properties. Usually, mechanically strong superporous hydrogels can be made by increasing the crosslinking density, but this would result in a very small extent of swelling with a loss of the superabsorbent property. Thus, it is desired to make superporous hydrogels having fast swelling and high absorbency characteristics as well as high mechanical strength.

SUMMARY OF THE INVENTION

The present invention is for a superporous hydrogel (SPH) composite, and related hydrogel composite, formed of an interpenetrating network of a polymer and particles of a fast water-absorbing material (a disintegrant), as defined hereinbelow. The polymer is formed of at least one ethylenically-unsaturated monomer and a multi olefinic crosslinking agent, and the polymer is further crosslinked to the disintegrant particles. A superporous hydrogel composite of the invention is characterized by having superabsorbence properties and mechanical strength, as exemplified by its swelling ratio and compression modulus, respectively. The SPH composite also has a very short swelling time.

A superporous hydrogel composite of the present invention has an average pore size in the range of 10 $\mu$m–3,000 $\mu$m, more preferably 50 $\mu$m–1,000 $\mu$m, and most preferably 100 $\mu$m–600 $\mu$m.

A superporous hydrogel composite of the present invention is formed in part from at least one ethylenically-unsaturated monomer. The monomer is preferably selected from (meth)acrylic acid, salts of (meth)acrylic acid, esters of (meth)acrylic acid, salts and acids of esters of (meth)acrylic acid, amides of (meth)acrylic acid, N-alkyl amides of (meth)

acrylic acid, salts and acids of N-alkyl amides of (meth) acrylic acid, N-vinyl pyrrolidinone, acrylamide, acrylamide derivatives (e.g., N-n-propylacrylamide, N-isopropylacrylamide), methacrylamide, methacrylamide derivatives (e.g., N-cyclopropylmethacrylamide), and the like, and mixtures thereof.

The superporous hydrogel composite is also formed from a crosslinking agent, which is preferably selected from BIS (N,N'-methylenebisacrylamide), ethylene glycol di(meth) acrylate, piperazine diacrylamide, glutaraldehyde, epichlorohydrin, and degradable crosslinking agents including crosslinkers containing 1,2-diol structures (e.g., N,N'-diallyltartardiamide), and functionalized peptides and proteins (e.g., albumin modified with vinyl groups).

A superporous hydrogel composite of the invention further is formed of particles of a disintegrant, as defined hereinbelow. Preferred disintegrants are crosslinked natural and synthetic positively and negatively charged polymers (polyelectrolytes) and neutral, hydrophilic polymers. Exemplary disintegrants include crosslinked sodium carboxymethylcellulose, crosslinked sodium starch glycolate, and crosslinked polyvinylpyrrolidone.

A superporous hydrogel composite of the invention is suitably formed by combining at least one ethylenically-unsaturated monomer, a multiolefinic crosslinking agent, particles of a disintegrant, and a blowing agent. This admixture is then subjected to polymerization and foaming conditions to polymerize and crosslink the monomer, crosslinking agent, and disintegrant, and to generate the superporous structure of the hydrogel composite.

BRIEF DESCRIPTION OF THE DRAWINGS

FIG. 5 illustrates time-lapse gastric retention of a superporous hydrogel or composite. Small dried superporous hydrogel (A) quickly swells in the stomach (B). It is slowly degraded in the stomach by mechanical or enzymatic degradation or both (C), and eventually emptied from the stomach (D). A swollen superporous hydrogel or superporous hydrogel composite remains in the stomach due to its large size. Gastric contraction (B-1→B-3) cannot empty the gel and it is bounced back into the body of the stomach (B-4 and B-5) and this sequence is repeated.

DETAILED DESCRIPTION OF THE INVENTION

Figure 1:
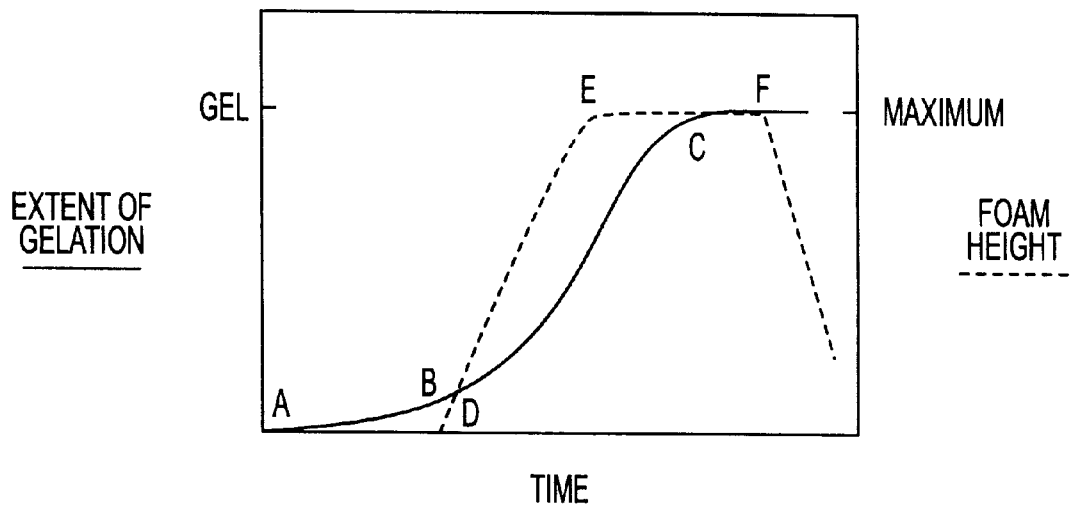
FIG. 1 illustrates the relative kinetics of gel formation by crosslinking polymerization (solid line) and foam formation (dotted line).

A method of forming an instant hydrogel composite comprises combining at least one ethylenically-unsaturated monomer, a multiolefinic crosslinking agent, and particles of a fast water-absorbing material (a disintegrant) to form an admixture thereof. The admixture is then subjected to polymerization conditions to produce the hydrogel composite.

A method of forming an instant superporous hydrogel (SPH) composite comprises combining the aforementioned components of a hydrogel composite, as well as a blowing agent, in an admixture. Whenever an SPH composite is desired, polymerization and foaming of the admixture preferably are performed simultaneously.

Preferably, the at least one ethylenically-unsaturated monomer, a multiolefinic crosslinking agent, and particles of a disintegrant are combined to form a first admixture, prior to combining this admixture with the blowing agent.

Preferred ethylenically-unsaturated monomers for use in the invention are selected from (meth)acrylic acid, salts of (meth)acrylic acid, esters of (meth)acrylic acid, salts and acids of esters of (meth)acrylic acid, amides of (meth)acrylic acid, N-alkyl amides of (meth)acrylic acid, salts and acids of N-alkyl amides of (meth)acrylic acid, N-vinyl pyrrolidinone, acrylamide, acrylamide derivatives (e.g., N-n-propylacrylamide, N-isopropylacrylamide), methacrylamide, methacrylamide derivatives (e.g., N-cyclopropylmethacrylamide), and the like, and mixtures thereof.

Particularly preferred monomers include acrylamide (AM), N-isopropylacrylamide (NIPAM), 2-hydroxyethyl methacrylate (HEMA), 2-hydroxypropyl methacrylate (HPMA), N-vinyl pyrrolidinone (VP), acrylic acid (AA), 2-acrylamido-2-methyl-1-propanesulfonic acid (AMPS), 3-sulfopropyl acrylate, potassium salt (SPAK), 2-(acryloyloxy)ethyltrimethyl-ammonium methyl sulfate (ATMS), inorganic salts thereof, and mixtures thereof.

A multiolefinic crosslinking agent employed in the invention is a monomer or a polymer containing at least two vinyl groups. Preferred crosslinking agents include BIS, ethylene glycol di(meth)acrylate, piperazine diacrylamide, glutaraldehyde, epichlorohydrin, and degradable crosslinking agents including crosslinkers containing 1,2-diol structures (e.g., N,N'-diallyltartardiamide), and functionalized peptides and proteins (e.g., albumin modified with vinyl groups).

Particles of a disintegrant used in the present invention are selected from crosslinked natural and synthetic polyelectrolytes, such as crosslinked sodium carboxymethylcellulose, crosslinked sodium starch glycolate, crosslinked sodium carboxymethyl starch, crosslinked dextran sulfate, crosslinked chitosan, crosslinked hyaluronic acid, crosslinked sodium alginate, crosslinked pectinic acid, crosslinked deoxyribonucleic acids, crosslinked ribonucleic acid, crosslinked gelatin, crosslinked albumin, polyacrolein potassium, sodium glycine carbonate, crosslinked poly(acrylic acid), crosslinked poly(styrene sulfonate), crosslinked poly(aspartic acid) and, crosslinked polylysine. Also, a crosslinked neutral, hydrophilic polymer, such as crosslinked polyvinylpyrrolidone, crosslinked ultramylopectin, crosslinked poly(ethylene glycol), crosslinked neutral cellulose derivatives, microcrystalline cellulose, powdered cellulose, cellulose fiber, and crosslinked starch can be used. Non-crosslinked forms of the above-mentioned polymers in particulate shapes, and porous, inorganic materials that provide wicking by capillary forces can also be used.

The ratio of crosslinking agent to monomer is preferably in the range of 0.01:100 to 10:100. The ratio of disintegrant to polymer is preferably in the range of 1:100 to 100:100.

Polymerization can be initiated photochemically, e.g., with a UV lamp, or chemically by combining the chemical initiator with the admixture prior to subjecting it to the polymerization and foaming conditions.

It is generally preferred that a foam stabilizing agent is combined with the admixture of monomer, crosslinking agent, and disintegrant, prior to subjecting the same to the polymerization and foaming conditions.

Various foaming techniques can be employed, such as by introducing gas bubbles from an external gas source, and as discussed herein. However, it is preferred to conduct the foaming by means of a blowing agent dissolved or dispersed in the admixture of monomer, crosslinking agent, and disintegrant. A particularly preferred blowing agent is sodium bicarbonate, $NaHCO_3$, admixed with an acid, such as acrylic acid, to initiate decomposition of the $NaHCO_3$ and produce gaseous bubbles of $CO_2$.

Suitable polymerization and foaming conditions as referred to herein include ambient pressure, and a temperature in the range of 5–90° C., more preferably ambient temperature. The time allowed for suitable polymerization and foaming is conveniently in the range of 20 seconds to 60 minutes.

A superporous hydrogel composite of the invention typically has an average pore size in the range of 10 $\mu$m to 3,000 $\mu$m, more preferably, in the range of 50 $\mu$m to 1,000 $\mu$m, and most preferably, in the range of 100 $\mu$m to 600 $\mu$m.

Superporous hydrogels and composites thereof represent a new kind of hydrogel having numerous large size pores inside them. Superporous hydrogels have numerous pores while conventional hydrogels show no pores throughout the matrix even when inspected with scanning electron microscopy (SEM). The typical size of pores in superporous hydrogels is larger than 100 $\mu$m, usually in the range of several hundreds micrometers, and can be up to the millimeter range. Most of the pores inside the superporous hydrogel are connected to form an open channel system. The size and number of the pores can be controlled by adjusting the type and amount of surfactant and gas forming agent during crosslinking polymerization. Even after drying, the pores of the superporous hydrogels remain connected to each other to form capillary channels. Because of this, dried superporous hydrogels can swell extremely fast upon contact with water and they can swell to a very large size.

It should be noted that superporous hydrogels have distinctly different properties compared to microporous and macroporous hydrogels. First, the size of pores in the superporous hydrogels can be made to range from as small as 10 $\mu$m to more than one millimeter, which is much larger than the pores in the microporous or macroporous hydrogels. Second, in contrast to conventional microporous or macroporous hydrogels, which contain a relatively small fraction of empty spaces, the superporous hydrogels can easily accommodate gas cells more than several hundred percent of the volume of the starting monomer mixtures. Third, pores in the superporous hydrogels remain connected even after drying, which enables the dried hydrogels to swell extremely fast.

The porous hydrogels can be prepared in the presence of gas bubbles. For instance, the monomers can be polymerized or water-soluble polymer chains can be crosslinked around gas bubbles generated by a blowing agent. Gas blowing technology has been widely used in the preparation of plastic foams using materials such as polyurethanes, rubber, and polyvinylchloride (PVC). The key ingredient in the foaming process is a "blowing agent" (or foaming agent) which is defined as any substance or combination of substances capable of producing a cellular structure within a polymer matrix. Foaming agents are classified as physical agents, which expand when pressure is released, such as nitrogen and carbon dioxide, and chemical agents, which decompose or react to form a gas, e.g., $NaHCO_3$, $Na_2CO_3$, and $CaCO_3$.

I. Preparation of Superporous Hydrogels

Recently, the gas blowing technique was used to prepare "superporous hydrogels" [Park, H. et al., 1994A; Park, H. et al., 1994B]. Because of the foaming technique used in the preparation of superporous hydrogels, they may also be called "hydrogel foams." In the synthesis of superporous hydrogels by the gas blowing technique, foaming and polymerization have to occur simultaneously, which makes it important to control the timing for foaming and polymerization. In the study mentioned above, inorganic carbonates, such as sodium carbonate and sodium bicarbonate, were used as a foaming agent.

The present inventors have successfully used the gas blowing technique to make superporous hydrogels of polyacrylamide, poly(sodium acrylate), poly(2-hydroxyethyl methacrylate), poly(hydroxypropyl methacrylate), poly(3-sulfopropyl acrylate, potassium salt), poly(2-acrylamido-2-methyl-1-propanesulfonic acid), poly({2-(acryloyloxy)ethyl}trimethylammonium methyl sulfate), poly(N-isopropyl acrylamide), poly(N-vinyl pyrrolidinone) (PVP), modified sucrose, and gelatin. Of course, many other superporous hydrogels can be made by this method. The pore size of the superporous hydrogels prepared by the foaming technique is usually larger than 100 $\mu$m, and it can easily reach the millimeter range. Usually, the pores are so large that they are visible with the unaided eye.

As mentioned above, superporous hydrogels are prepared by crosslinking polymerization of monomers in the presence of gas bubbles. Thus, synthesis of superporous hydrogels requires blowing agents and surfactants, in addition to the usual components for making hydrogels such as monomer, crosslinker, and chemical initiator. Blowing agents generate the gas bubbles and surfactants stabilize the generated foams by lowering the film-air interfacial tension and increasing the film viscosity [Hartley, F. D. et al., 1968].

There are two processes involved in the preparation of superporous hydrogels: polymerization and foaming. In order to make homogeneous superporous hydrogels, these two processes should occur about the same time. Thus, control of timing of the two processes is critical. To permanently capture the gas bubbles in the polymer network, the gelling must occur when the foam is stabilized. Since the foaming process is relatively short and it is difficult to stabilize a foam longer than a few minutes, gelling has to start within a few minutes after the beginning of foaming, e.g., the addition of $NaHCO_3$ to the monomer mixture.

Fast gelling can be achieved by careful choice of monomers (type and concentration), initiators (type and concentration), temperature, and solvent. Typically, water soluble acrylates, methacrylates, and acrylamides gel very fast. Accordingly, it is preferred that superporous hydrogels are made from these monomers. In addition, high monomer concentration, proper type of initiator, high initiator concentration, high temperature, and good solvent can all increase the polymerization rate.

Gas bubbles can be formed by any gas blowing method, either chemical or mechanical. In the present study, $NaHCO_3$ is selected as a blowing agent because of its unique advantages (as described below) that may not be provided by other techniques, such as thermal decomposition of chemical agent, mechanical whipping, volatilization of low-boiling liquid, chemical reaction, expansion of dissolved gas upon pressure release, incorporation of microspheres into a polymer mass, and expansion of gas-filled beads by heating [Klempner, D. et al., 1991]. The amount of blowing agent used controls the pore size and the porosity of superporous hydrogels.

For large-scale production of superporous hydrogels, mechanical blowing through one or more atomizers may be a better choice than the chemical blowing method. This is because it may not be desirable to complete a polymerization in a few minutes since the heat generated during polymerization may not be dissipated quickly. Thus, a smaller amount of initiator may be used to delay the gelling time (e.g., more than 10 minutes). Since mechanical blowing can start at any time for any duration, the foaming process may begin at the desired time and foam height can be maintained as necessary. Accurate timing control is possible by mechanical blowing in the large-scale production of superporous hydrogels.

A. Preparation of Superporous Hydrogels in Aqueous Solution All monomers and chemicals, unless otherwise specified, were obtained from Aldrich Chemical Company, Inc. (Milwaukee, Wis.). Superporous hydrogels are synthesized from various monomers, such as acrylic acid (AA), acrylamide (AM), hydroxypropyl methacrylate (HPMA) (Eastman Kodak Chemical Co.), N-isopropyl acrylamide (NIPAM), vinylpyrrolidone (VP), hydroxyethyl methacrylate (HEMA), 3-sulfopropyl acrylate (potassium salt, SPAK), 2-acrylamido-2-methyl-1-propanesulfonic acid (AMPS), and {2-(acryloyloxy)ethyl}trimethylammonium methyl sulfate (ATMS). To ensure fast gelling, the concentration of monomers in aqueous solution was above 10% in most cases. The molecular structures of selected monomers used in this study are shown in Table 1.

TABLE 1

Vinyl monomers used for making superporous hydrogels.

| Chemical name (and abbreviation) | Monomer structure |
|---|---|
| Acrylamide (AM) | |
| N-isopropylacrylamide (NIPAM) | |
| 2-hydroxyethyl methacrylate (HEMA) | |

TABLE 1-continued

Vinyl monomers used for making superporous hydrogels.

| Chemical name (and abbreviation) | Monomer structure |
|---|---|
| 2-hydroxypropyl methacrylate (HPMA) | |
| N-vinyl pyrrolidinone (VP) | |
| Acrylic acid (AA) | |
| Sodium acrylate | |
| 2-acrylamido-2-methyl-1-propanesulfonic acid (AMPS) | |
| 3-sulfopropyl acrylate, potassium salt (SPAK) | |
| 2-(acryloyloxy)ethyltrimethyl-ammonium methyl sulfate (ATMS) | |

The redox pair of ammonium persulfate (APS) and N,N,N',N'-tetramethylethylenediamine (TEMED) (Bio-Rad; Richmond, Calif.) are preferably used as initiators, while N,N'-methylenebisacrylamide (BIS) is used as a cross-linker. The amount of crosslinker is equivalent to 0.01% (w/w) to 10% (w/w) of the monomer. In most of the superporous hydrogel preparations, the cross-linker concentration is equivalent to about 1% (w/w) of monomer. Too high cross-linker concentrations caused the swollen superporous hydrogels to become more brittle and to result in reduced swelling ratio. On the other hand, too low cross-linker concentrations caused the superporous hydrogels to become more soft and fragile. The initiator concentration can significantly affect the polymerization rate. Typically, the concentrations of APS and TEMED are about 2% (w/w) of monomer. Gelling usually starts within a few minutes after the addition of $NaHCO_3$.

Preferably, $NaHCO_3$ (Mallinckrodt; Paris, Ky.) is used as a blowing agent in the presence of an acid (acrylic acid, HCl, citric acid, or acetic acid) for the preparation of superporous hydrogels because the $NaHCO_3$-acid system exhibits advantages over other gas blowing techniques. It is safe, cheap, and easy to use. More importantly, it allows one to control the timing of bubble formation and the amount of gas introduced during the polymerization step. First, the monomer, crosslinker, acid, surfactant, and initiators are mixed. Then, NaHCO$_3$ is added to generate the gas bubbles. The foam size is determined by the amount of released gas bubbles which, in turn, is determined by the amount of acid and NaHCO$_3$.

As shown in FIG. 1, two processes are involved in the superporous hydrogel preparation. The solid line A-B-C represents the polymerization process, and the dotted line D-E-F represents the foaming process. When APS/TEMED are used as initiators, the polymerization rate is pH-dependent. The optimal pH for the initiators is 7–8. Under this pH range, the polymerization proceeds rapidly after the addition of initiator, and gelling can start usually after 1–2 minutes. If foaming starts too late, the solution can become too viscous for good mixing, and it results in a non-homogeneous porous hydrogel.

To make a homogeneous superporous hydrogel, the time for the addition of the foaming agent must be carefully controlled over a very narrow viscosity range. Usually, this timing control is difficult. However, when acid and NaHCO$_3$ are used as the foaming agents, they provide a special trigger system that makes the timing control very easy.

In the beginning of polymerization (point A), all the ingredients for polymerization, except NaHCO$_3$, are mixed. The presence of acid lowers the pH to an acidic level (pH 5–6). Therefore, the TEMED-catalyzed free radical generation is inhibited because TEMED is protonated under this pH. This results in a very slow polymerization (A—B). At point D, NaHCO$_3$ is added, which reacts with the acid and starts the foaming process (DEE). In the meantime, the pH of the solution rises to a pH above the neutral level (i.e., pH 7–8) due to the neutralizing effect of NaHCO$_3$. At this pH, TEMED (in the free base form) can catalyze free radical generation from ammonium persulfate and start the accelerated polymerization [Gordon, A. H., 1971].

The gelation proceeds rapidly (B→C) and is completed at point C. Here, NaHCO$_3$ acts as a trigger for polymerization so that the foaming and polymerization can proceed in parallel. Therefore, no special timing control is needed. From E to F. the foam stays at its maximum size in the presence of foam stabilizers. After point F, the foam subsides (if gelling does not occur). To make a good superporous hydrogel, the gelling should start when the foam is maintained in its maximum size. In other words, point C should be between points E and F. Accordingly, in the present method, gelling typically occurs 1–2 minutes after the addition of NaHCO$_3$ so that the foam is stabilized until gelling is started. An excess amount of NaHCO$_3$ should be used to ensure that the final pH is above neutral, and to control the foam volume by the amount of acid.

In general, the polymerization process is slow and the duration of maximum foaming (E→F) is short. Preferred monomers used in the synthesis of superporous hydrogels are acrylates and their derivatives, because they have a relatively fast polymerization rate. The APS/TEMED system used in this study initiated the gelling of these monomers within a few minutes. To prolong maximum foaming during the gelling process, various foam stabilizers are preferably used.

A good foam stabilizer should be able to stabilize the foam until the beginning of the gelling process. More than thirty different kinds of surfactants have been examined, such as Triton surfactants, Tween and Span surfactants, Pluronic® surfactants (poly(ethylene oxide)-poly(propylene oxide)-poly(ethylene oxide) tri-block copolymers) (BASF), Silwet® surfactants (OSi Specialties Inc.), sodium dodecyl sulfate (Bio-Rad Laboratories), albumin (Sigma Chemical Company), and gelatin. Of these, Pluronic® F127 (PF127) showed the best foam stabilizing property for most of the hydrophilic monomers used in the superporous hydrogel preparation. PF127 sustained the foam for the longest period of time. For relatively hydrophobic monomers, such as NIPAM or HPMA, PF127 alone did not provide good foam stabilizing effect. However, a combination of PF127, Pluronic® P105 (PP105), and Silwet® 7605 (SL7605) provided a satisfactory foam stabilizing effect. SL7605 is a polyalkyleneoxide-modified polydimethylsiloxane surfactant. It was observed that too little surfactant could not provide enough foam stabilizing effect, but excess surfactant above a certain level did not result in better foam stabilizing effect. Surfactant concentrations at 0.5% (w/v) of the total solution were found to be adequate.

Proteins do not have a vinyl group, so their polymerization cannot be catalyzed by a chemical initiator. However, proteins have free amine groups which can be crosslinked by glutaraldehyde. Therefore, superporous protein hydrogels can still be made by the gas blowing method. Superporous gelatin hydrogels were made as an example (Example 14).

B. Preparation of Superporous Hydrogels in Organic Solvents

Relatively hydrophobic monomers such as 2-hydroxypropyl methacrylate (HPMA) and some of the modified sucrose monomers [Chen, J., 1997] do not dissolve in aqueous solution. Therefore, organic solvents need to be used to make their superporous hydrogels. Dimethyl sulfoxide (DMSO) (Fisher Scientific) can be used to make superporous hydrogels from modified sucrose monomers, and isopropanol can be used for making PHPMA superporous hydrogel. A proper solvent should accommodate the solubility of monomer, crosslinker, foaming agent, foam stabilizer, and initiator. BIS crosslinker is soluble in both isopropanol and DMSO. In DMSO, NaHCO$_3$ does not generate gas bubbles when mixed with acrylic acid, acetic acid, HCl, or citric acid. However, NaHCO$_3$ becomes a good gas foaming agent in DMSO or isopropanol when mixed with p-tolunenesulfonic acid, a strong organic acid.

As mentioned above, PF127 is an excellent foam stabilizer for most of the hydrophilic monomers in aqueous solution. For relatively hydrophobic monomers or in organic solvent, PF127 alone did not provide a good foam stabilizing effect. However, a proper combination of PF127, PP105, and SL7605 provides a satisfactory foam stabilizing effect. As discussed in Example 15, the APS/TEMED system was used as the initiators. However, a series of azo initiators (Wako Chemical Co.) having different decomposition rates and different solubilities in organic solvent were found to be better candidates than APS/TEMED for the preparation of hydrophobic superporous hydrogels in organic solvent.

Not all of the hydrophobic superporous hydrogels showed significant swelling in water as expected. They are most suitable for improving the mechanical strength of the hydrophilic superporous hydrogels by making interpenetrating networks. Hydrophobic monomers can also be mixed with hydrophilic monomers before synthesizing the superporous hydrogels to make copolymers.

The following examples illustrate, but do not limit, the present invention.

EXAMPLES

Example 1

Polyacrylamide (PAM) superporous hydrogel

The following components were added sequentially to a test tube (20 mm outer diameter×150 mm in length): 1000

μl of 50% AM; 200 μl of 2.5% BIS; 460 μl of distilled deionized water (DDW); 100 μl of 10% Pluronic® F127; 25 μl of AA; 40 μl of 20% APS; and 40 μl of 20% TEMED. The test tube was shaken to mix the solution after each ingredient was added. Finally, 90 mg of NaHCO$_3$ powder was added and vigorously stirred using a spatula for 5–10 seconds to accelerate foaming and to evenly distribute the gas bubbles. The gelling started within 1–2 minutes of adding NaHCO$_3$.

Example 2

Poly(sodium acrylate-co-acrylic acid) superporous hydrogel

The monomer solution was prepared by partially neutralizing acrylic acid with NaOH solution to make a final pH of 6 and the final monomer solution equivalent to 6 M of total acrylic acid and acrylate.

The following components were added sequentially to a test tube (20 mm outer diameter×150 mm in length): 1000 μl of monomer solution; 200 μl of 2.5% BIS; 460 μl of distilled water; 100 μl of 10% Pluronic® F127; 25 μl of AA; 40 μl of 20% APS; and 40 μl of 20% TEMED. The test tube was shaken to mix the solution after each ingredient was added. Finally 90 mg of NaHCO$_3$ was added, and the whole solution was stirred vigorously using a spatula for 5–10 seconds to accelerate foaming and to evenly distribute the gas bubbles. The gelling started within 1–2 minutes.

Example 3

Poly(2-hydroxyethyl methacrylate) (PHEMA) superporous hydrogel

Because hydroxyethyl methacrylate (HEMA) has a slower polymerization rate than those acrylate monomers used in Examples 1 and 2, a higher temperature (63° C.) was used to promote the polymerization rate.

700 μl of HEMA, 100 μl of 2.5% BIS, and 100 μl of 10% Pluronic® F127 were added to a test tube (13 mm diameter× 100 mm length), and the whole solution was warmed to 63° C. To this solution were added 50 μl of 20% APS and 50 μl of 20% TEMED. After maintaining the temperature at 63° C. for 80 sec, 80 mg of NaHCO$_3$ was added and vigorously stirred using a spatula for 5–10 seconds to accelerate foaming and to evenly distribute the gas bubbles. Gelling started within 1–2 minutes of adding NaHCO$_3$.

In this formulation, no acid was added. Gas bubbles were generated when NaHCO$_3$ was added after the monomer mixture had reacted for 80 seconds at 63° C. Early addition of NaHCO$_3$ did not generate gas bubbles. The reason for this is not clear. One possible reason is that gas bubbles were generated by the decomposition of NaHCO$_3$ from the heat of polymerization. If the addition of NaHCO$_3$ was too late, the viscosity of the solution became too high for a good mixing. The result was a non-uniform superporous hydrogel with low porosity. When NaHCO$_3$ was added after the start of gelling, no foam was generated at all.

Example 4

Poly(3-sulfopropyl acrylate, potassium salt) (PSPAK) superporous hydrogel

The following components were added sequentially to a test tube (13 mm outer diameter×100 mm length): 1000 μl of 30% SPAK; 40 μl of 2.5% BIS; 50 μl of 10% Pluronic® F127; 25 μl of AA; 20 μl of 20% APS; and 20 μl of 20% TEMED. The test tube was shaken to mix the solution after each ingredient was added. Finally 90 mg of NaHCO$_3$ was added, and the whole solution was stirred vigorously using a spatula for 5–10 seconds to accelerate foaming and evenly distribute the gas bubbles. PSPAK is a strong anionic polymer (polyelectrolyte), and is charged even under acidic pH.

Example 5

Poly{2-(acryloyloxy)ethyl trimethylammonium methyl sulfate} (PATMS) superporous hydrogel The following components were added sequentially to a test tube (13 mm outer diameter×100 mm length): 1000 μl of 30% ATMS; 40 μl of 2.5% BIS; 50 μl of 10% Pluronic® F127; 25 μl of AA; 20 μl of 20% APS; and 20 μl of 20% TEMED. The test tube was shaken to mix the solution after each ingredient was added. Finally 90 mg of NaHCO$_3$ was added, and the whole solution was stirred vigorously using a spatula for 5–10 seconds to accelerate foaming and to evenly distribute the gas bubbles.

Example 6

Poly(2-acrylamido-2-methyl-1-propanesulfonic acid) (PAMPS) superporous hydrogel

The monomer solution was prepared by partially neutralizing AMPS with NaOH solution to make a final pH of 5 and the final monomer solution at 30% (w/w).

The following components were added sequentially to a test tube (13 mm outer diameter×100 mm length): 1000 μl of partially neutralized monomer solution; 40 μl of 2.5% BIS; 50 μl of 10% Pluronic® F127; 25 μl of AA; 20 μl of 20% APS; and 20 μl of 20% TEMED. The test tube was shaken to mix the solution after each ingredient was added. Finally 90 mg of NaHCO$_3$ was added, and the solution was stirred vigorously using a spatula for 5–10 seconds to accelerate foaming and to evenly distribute the gas bubbles.

Example 7

Poly(N-vinyl pyrrolidinone) (PVP) superporous hydrogel

The polymerization rate of 1-vinyl-2-pyrrolidinone (VP) is slower than that of acrylate or methacrylate monomer. The APS/TEMED initiators were not effective in initiating polymerization of VP monomer even at 60° C. for several hours. It was observed, however, that V545 (a water-soluble azo-initiator from Wako Pure Chemical Industries, LTD, Japan.) initiated polymerization of VP monomer in less than a minute at 60° C. in aqueous solution. Since fast gelling was required for the superporous hydrogel preparation, V545 was used as the initiator in the PVP superporous hydrogel preparation.

The following components were added sequentially to a test tube (13 mm outer diameter×100 mm length): 500 μl of VP; 200 μl of 2.5% BIS; 100 μl of water; 50 μl of 10% Pluronic® F127; and 20 μl of AA. The test tube was shaken to mix the solution after each ingredient was added. After warming in a 85° C. water bath for 2 min, 50 μl of freshly made 10% aqueous V545 solution was added and mixed again. Immediately, 20 mg of NaHCO$_3$ was added and the whole solution was stirred vigorously using a spatula for 5–10 seconds to evenly distribute the gas bubbles. The solution was kept at 85° C. for 5 minutes.

At 85° C., the polymerization of VP proceeded very fast, and the gelling started within 1 minute after the addition of V545. Unlike the redox APS/TEMED initiators used in Examples 1–6, the radical generation in this formulation was based on the thermo-decomposition of V545. Thus, the polymerization was not a pH dependent process. Since the trigger system provided by acid/NaHCO$_3$ did not exist in this formula, more accurate timing control was required to make PVP superporous hydrogels. NaHCO$_3$ should be added right after the addition of V545. Since the polymerization initiated by V545 is not pH dependent, it can be used to make superporous hydrogels directly from acidic monomers (without neutralization).

Example 8

Poly(acrylic acid) (PAA) superporous hydrogel

In Example 2, to make superporous hydrogels from acrylic acid, the acidic monomer, acrylic acid, had to be neutralized first. Otherwise, the pH of the monomer solution would be too low, and thus the polymerization rate would be too slow when APS/TEMED were used as initiators. However, since V545 can initiate the polymerization even at an acidic condition, PAA superporous hydrogels can be made without the neutralization step.

The following components were added sequentially to a test tube (13 mm outer diameter×100 mm length): 500 µl of AA; 200 µl of 2.5% BIS; 500 µl of water; 100 µl of 10% Pluronic® F127. The test tube was shaken to mix the solution after each ingredient was added. After warming in a 85° C. water bath for 2 min, 100 µl of 10% V545 was added and mixed again. Within 15 seconds after the addition of V545, 15 mg of NaHCO$_3$ was added and the whole solution was stirred vigorously using a spatula for 5–10 seconds to evenly distribute the gas bubbles. The solution was kept at room temperature for 5 minutes.

Example 9

Poly(acrylic acid-co-acrylamide) (poly(AA-co-AM)) superporous hydrogel

The monomer mixture was prepared by adding 13 ml of AA, 9.6 g of AM, 5.81 ml of 2.5% BIS, approximately 6 g of NaOH (to adjust the final pH to about 5.1) and water to make the final volume of 100 ml.

The superporous hydrogels were prepared in a plastic test tube (17 mm in diameter×100 mm in length) by mixing 1.5 ml of monomers, 100 µl of 10% PF127, 50 µl of 20% APS, 50 µl of 20% TEMED, and water (to make the final volume of 2 ml). The test tube was shaken to mix the solution after each ingredient was added. Finally 120 mg of NaHCO$_3$ was added, and the whole solution was vigorously stirred using a spatula for 10 seconds to accelerate foaming and to evenly distribute the gas bubbles. The superporous hydrogel was then cured at room temperature for 10 min. The final monomer concentration in this preparation was about 17.4% (w/v) and the BIS concentration was 0.3 mol % of the total monomers. The foam heights in the test tubes (17 mm outer diameter) right after gelling ranged from 6.5 cm to 7 cm.

Example 10

Poly(AM-co-SPAK)-(Ac-Di-Sol®) superporous hydrogel composites

Poly(AM-co-SPAK) superporous hydrogel was prepared in a glass test tube (outer diameter of 22 mm, inner diameter of 19 mm, and height of 175 mm). The following components were added sequentially to the test tube: 1,200 µl of 50% acrylamide (AM); 900 µl of 50% 3-sulfopropyl acrylate potassium salt (SPAK); 450 µl of 2.5% BIS; 90 µl of 10% Pluronic® F127; 30 µl of 50% (v/v) acrylic acid; 45 µl of 20% ammonium persulfate. The test tube was shaken to mix the solution after each ingredient was added. Then 270 mg Ac-Di-Sol® powder was added to the mixture and stirred using a spatula to mix them. After this, 45 µl of 20% TEMED was added to the mixture and the test tube was shaken again to mix it. Finally, 100 mg of NaHCO$_3$ powder was added and the mixture was immediately stirred vigorously using a spatula for 10 sec. The superporous hydrogel was cured at room temperature for 10 min. Then the superporous hydrogel was retrieved (pinched) from the test tube using two spatulas, and washed in 1 liter beaker containing 400 ml simulated gastric fluid (SGF, pH 1.2 based on USP) for 24 h. This step was called acidification. After this, the superporous hydrogel was dried at room temperature for 5 days.

The total amount of acid used in Example 10 is very small compared with that used in other examples, and thus the total amount of gas bubbles generated were also small. Since it is desirable to have superporous hydrogels with a well-connected and uniformly-distributed intercellular capillary channel system (which is essential for fast swelling), the limited amount of gas bubbles needs to be well preserved during the preparation. To examine the foam stabilizing effect of Ac-Di-Sol®, four types of superporous hydrogels were prepared based on Example 10: (A) in the absence of Pluronic® F127; (B) in the absence of Ac-Di-Sol®; (C) in the presence of both Pluronic® F127 and Ac-Di-Sol®; (d) in the absence of Ac-Di-Sol® but with two times more acrylic acid (AA) (i.e., 60 µl instead of 30 µl of 50% AA). Only sample (C) had a high swelling rate and good mechanical strength, indicating the presence of the interconnected pores. SEM pictures showed interconnected pores in Sample (C). This study clearly shows that Ac-Di-Sol® is important in making interconnected channels in superporous hydrogels whenever a small amount of blowing agent is employed.

Example 11

Poly(N-isopropyl acrylamide-co-acrylamide) (poly(NIPAM-co-AM)) superporous hydrogels Three types of poly(NIPAM-co-AM) superporous hydrogels were synthesized. The molar ratios of NIPAM to AM in these superporous hydrogels were 9:1, 8:2, and 7:3, and the superporous hydrogels were labeled for convenience as N90, N80, and N70, respectively. The superporous hydrogels were prepared in a glass test tube (20 mm in diameter× 150 mm in length). The total monomer concentration was 1.34 M, and the total solution was 1.66 ml. The ratio of BIS crosslinker to total monomer was 1 mol %.

Monomers, crosslinker (3.43 mg of BIS), foam stabilizers, 6 N HCl (50 µl), and initiators (10 mg each of APS and TEMED) were added and mixed sequentially in a test tube. NaHCO$_3$ (60 mg) was added last, and the mixture was vigorously stirred using a spatula to accelerate foaming and to evenly distribute the gas bubbles.

In one sample, both PF127 (10 mg) and Silwet®7605 (SL7605) (3 mg) were used as foam stabilizers. SL7605 was first dissolved in dimethyl sulfoxide to make a 10% solution. When only one surfactant, either PF127 or SL7605, was used for the sample, the foam did not last long enough to make a uniform hydrogel foam. In other samples, however, only 10 mg of PF127 was used as the foam stabilizer, since PF127 alone stabilized the foam quite well due to the increased hydrophilicity of the higher amount of AM.

Example 12

Poly (AA-co-AM)-(Ac-Di-Sol®) superporous hydrogel composites

Superporous hydrogels containing Ac-Di-Sol® were made by adding Ac-Di-Sol® to the formulation in Example 9. Before the addition of TEMED, 50–200 mg of Ac-Di-Sol® powder was added to the solution and the mixture was stirred using a spatula to evenly distribute Ac-Di-Sol®. The Ac-Di-Sol® swelled in the solution and made the solution viscous. After TEMED and $NaHCO_3$ were added, the mixture was stirred vigorously using a spatula for 10 seconds to accelerate foaming and to evenly distribute Ac-Di-Sol® and the gas bubbles.

Example 13

PAM—Primojel® superporous hydrogel composite

To make superporous hydrogels containing Primojel®, the following components were added sequentially to a glass test tube (20 mm outer diameter×150 mm length): 600 μl of 50% AM; 120 μl of 2.5% BIS; 100 mg Primojel®; 240 μl of 10% Pluronic® F127; 700 μl of DDW; 100 μl of 6N HCl; 70 μl of 20% APS; and 70 μl of 20% TEMED. The test tube was stirred using a spatula to mix the solution after each ingredient was added. Finally 100 mg of $NaHCO_3$ was added, and the whole solution was stirred vigorously using a spatula for 5–10 seconds to accelerate foaming and to evenly distribute the gas bubbles.

Example 14

Gelatin superporous hydrogel

The following components were added to a test tube (13 mm outer diameter×100 mm length): 1 ml of 10% gelatin; 50 μl of 15% $MgCl_2$; 20 μl of 50% (v/v) AA. After the mixture was warmed to 85° C., 40 μl of 6% glutaraldehyde and a suspension containing 15 mg of $NaHCO_3$ were added, and the whole solution was stirred vigorously using a spatula for 5–10 seconds and left at 85° C. for 10 min.

For the preparation of gelatin superporous hydrogels, glutaraldehyde was used as a cross-linker. $MgCl_2$ was the catalyst for polymerization. Gelatin concentration higher than 10% is not recommended because the viscosity becomes too high for good mixing. Since the crosslinking reaction was too slow at room temperature, 85° C. was used to accelerate the crosslinking reaction. No surfactant was needed because the gelatin itself acted as a surfactant in this formulation. $NaHCO_3$ (15 mg) was first mixed with 15 μl of water to make a suspension before it was added to the solution. This was because $NaHCO_3$ in the suspension state could be mixed faster in the solution than $NaHCO_3$ in the dry state. Unlike the superporous hydrogels made from the acrylate monomers, the gelatin foam collapsed after it was cured.

Example 15

Poly(2-hydroxypropyl methacrylate) (PHPMA) superporous hydrogel

The following components were added sequentially to a test tube (13 mm outer diameter×100 mm in length): 500 μl of HPMA; 200 μl of 10% BIS (in DMSO); 90 μl of 10% Silwet® L7605 (in DMSO); and 30 μl of 5% Pluronic® P105 (in DMSO). The test tube was shaken to mix the solution after each ingredient was added. After warming in a 80° C. water bath, 180 μl of 10% APS (in water) and 90 μl of 10% TEMED (in water) were added and mixed again. After 30 seconds at 80° C., 30 mg of $NaHCO_3$ was added and the whole solution was stirred vigorously using a spatula for 5–10 sec. In the above formulation, 500 μl of HPMA can be replaced with 500 μl of 50% HPMA in isopropanol.

In the above experiments, no acid was added. Gas bubbles were generated when $NaHCO_3$ was added after the monomer mixture had reacted for 30 seconds at 80° C. Addition of $NaHCO_3$ prior to 30 seconds did not generate gas bubbles. The reason for this is not clear, but one possible reason is that the gas bubbles were generated with the decomposition of $NaHCO_3$ by the heat of the polymerization. The combination of the two foam stabilizers was important, since any one of them alone did not provide a good foam stabilizing effect.

Example 16

Superporous hydrogels with mucin coating on the surface

Another important property of the superporous hydrogels useful in many applications is slipperiness of the surface. The surface of superporous hydrogels was modified with mucin (Sigma Chemical Company, type II, crude, from porcine stomach) to increase the surface slipperiness.

The superporous hydrogels prepared in Example 10 (poly (AM-co-SPAK) superporous hydrogels) were acidified and dried. The rough side (i.e., the side that did not face the glass test tube during synthesis) was trimmed using a razor blade to remove the rough surface. The superporous hydrogels were then coated with 10% mucin solution (Sigma Chemical Company, type II, crude) using a cotton swab. The coated superporous hydrogels were heated in a 130° C. oven for 40 min. The coating and heating processes were repeated twice more. Heating albumin emulsion at 100–160° C. has been used to make crosslinked albumin microspheres [Arshady, R., 1990]. At high temperature, protein forms crosslinked networks. Mucin crosslinked on the surface of the superporous hydrogels at 130° C. to provide a slippery surface property. The slipperiness was retained even after the coated superporous hydrogels were washed in simulated gastric fluid (SGF) for more than two days. On the other hand, if the mucin-coated superporous hydrogels were not heated but dried at room temperature, the slipperiness was maintained for only one hour because the surface mucin was not crosslinked and was dissolved in SGF.

II. Swelling Properties of Superporous Hydrogels

A. Fast Swelling of Superporous Hydrogels

According to the kinetics of the swelling of a gel [Tanaka, T. et al., 1979], the characteristic time of swelling (τ) is proportional to the square of the characteristic length of the gel (L) and is inversely proportional to the diffusion coefficient of the gel network in the solvent (D) as follows:

$$\tau = L^2/D$$

The characteristic length for a spherical hydrogel is the radius, and for a hydrogel sheet is the thickness. The diffusion coefficient of hydrogel networks is on the order of $10^{-7}$ $cm^2$/sec [Kabra, B. G. et al., 1994; Tanaka, T. et al., 1979]. A 1 mm-thick gel slab with a diffusion coefficient of $10^{-7}$ $cm^2$/sec will take over an hour to reach 50% of the equilibrium swelling and more than six hours to reach 90% of equilibrium [Gehrke, S. H. et al., 1993]. This is far too slow for the gels to be used in practical applications, such as superabsorbents in baby diapers. To make fast swelling superabsorbent polymers (SAPs), submillimeter size gels in a powder form are commonly used in industry. The restriction on the size of the gels limits useful application of the SAP, and certainly SAP with a larger dimension would be highly desirable [Knack, I. et al., 1991].

The total swelling time for a dried superporous hydrogel in aqueous solution is determined by two factors: $t_1$ and $t_2$. $t_1$ is the time for water to reach all the surface of the pores in the superporous hydrogels. It is determined by the effectiveness of the capillary action in a superporous hydrogel. $t_2$ is the actual swelling time of the polymer matrix which is determined by the thicknesses of the cell walls and struts. Because the thicknesses of the cell wall and strut of superporous hydrogels are very thin, ranging from less than a micrometer to tens of micrometers, they have a very short characteristic swelling time. For superporous hydrogels, $t_2$ is comparable to that of an ultra-thin hydrogel film. The capillary action is mainly determined by the availability of capillary channels and the wettability of the channels. Various approaches have been attempted to maintain good capillary action (i.e., to decrease $t_1$) by maintaining open intercellular channels and good surface wettability.

B. Density and Swelling Ratio Measurement

As described in Example 9, partially neutralized acrylic acid (AA) and acrylamide (AM) were used as monomers. The degree of neutralization of AA by NaOH was 70% to 100%. The molar ratio of AA to AM was 5:4. BIS was used as a crosslinker and its concentration was 0.3 mol % of the total monomer. These numbers were chosen according to one formula used in the diaper industry [Takeda, H. et al., 1985]. The final monomer concentration in this preparation was about 17.4% (w/v) and the BIS concentration was 0.3 mol % of the total monomers.

After the superporous hydrogels were prepared, they were treated by different processes. The effects of these processes on the density, swelling ratio, and swelling time of superporous hydrogels were studied. In addition, effects of different additives on the swelling properties of superporous hydrogels were examined. These data are given in Table 2.

The density (d) of the dried superporous hydrogels was calculated by: $d = W_d/V_d$, where $W_d$ is the weight of a dried superporous hydrogel and $V_d$ is the volume of the dried superporous hydrogel. Since some of the dried superporous hydrogels lost their cylindrical shape after drying, direct measurement of their volumes was difficult. $V_d$ was determined by a solvent displacing method. Briefly, a dried superporous hydrogel was forced to submerge underneath the surface of hexane in a graduate cylinder using tweezers and then was quickly removed from hexane. The volume change read from the graduate cylinder before and after the removal was the volume of the dried superporous hydrogel. The accuracy of this method is about the same as using a ruler to measure the diameter and length of a regularly shaped superporous hydrogel. Hexane was used because it was very hydrophobic so that the superporous hydrogels did not swell and absorb the solvent.

For the swelling study, deionized distilled water (DDW) was used as the swelling medium. Each superporous hydrogel was cut into a disk shape with the diameter about twice as much as the height (for instance, Sample #4 in Table 2 had a diameter of 0.8 cm and height of 0.4 cm and weight ranging from 50 mg to 65 mg). Since superporous hydrogels became too fragile to handle after being swollen, the swelling ratio Q was determined by the sieve method.

The swelling ratio, Q, is defined as:

$$Q = (W_s - W_d)/W_d$$

where $W_s$ is the weight of the swollen superporous hydrogel and $W_d$ is the weight of the dried superporous hydrogel. A superporous hydrogel was placed on a sieve weighing boat. The sieve weighing boat containing the superporous hydrogel was immersed in distilled, deionizing water (DDW) to let the superporous hydrogel swell to equilibrium. To measure Q, the boat was taken out to drain the free water from the sieve and a paper towel was used to remove excess water from underneath the sieve. Then the weight of the swollen superporous hydrogel was measured by subtracting the boat weight from the whole weight. This method avoided direct handling of the fragile superporous hydrogels.

The swelling time is the time for a superporous hydrogel to reach the equilibrium swollen state when placed in the swelling medium, DDW.

C. Comparison of Non-porous Hydrogels and Superporous Hydrogels

Non-porous hydrogels (Sample #1 in Table 2) were prepared by the same formula used for superporous hydrogel preparation except no PF127 and $NaHCO_3$ were added. Sample #2 was prepared based on the formula described in Example 9. After polymerization, superporous hydrogels were retrieved using a spatula from the test tube and dried in a 55° C. oven for a day. In Sample #3, the retrieved superporous hydrogels were allowed to swell in DDW to equilibrium and washed several times in DDW. Then the washed superporous hydrogels were dried in a 55° C. oven for a day. This step removed the water-soluble components remaining in the superporous hydrogels such as foam stabilizer PF127. The absence of such water-soluble components is expected to affect the extent of collapse of the superporous hydrogels during drying due to the increased surface tension to that of pure water.

Due to the porous structures, Samples #2 and #3 had density of 0.76 and 0.80 $g/cm^3$, respectively, which were smaller than that of the non-porous gels (1.30 $g/cm^3$). Samples #2 and #3 also had higher swelling ratios (Q=328 and 307, respectively) than that of the non-porous hydrogel (Q=173). Again, this was due to the porous structures of superporous hydrogels. Water could be held in the open pores so that the overall water absorbency was higher for the superporous hydrogels. Samples #2 and #3 swelled much faster (31 min and 51 min, respectively) than the non-porous hydrogels (720 min). Sample #3 had a longer swelling time than Sample #2, possibly because of wettability differences in Samples #2 and #3. Since Sample #2 was not washed, there were water soluble ingredients, such as PF127, left on the surface of the superporous hydrogels. These ingredients might have changed the wettability so that Sample #2 swelled faster than Sample #3.

Although the superporous hydrogels in Samples #2 and #3 swelled much faster than conventional, non-porous hydrogels, their swelling time was still far slower than expected. The time-limiting step for the swelling of these superporous hydrogels was found to be the water penetrating step (i.e., $t_1$). It took almost all the swelling time for water to reach the center of a superporous hydrogel. After the water reached the center of the superporous hydrogels, they quickly swelled to their equilibrium sizes. This meant $t_2$ was very short in the superporous hydrogel, but $t_1$ was very long. To decrease the total swelling time, $t_1$ must be deceased. Therefore, subsequent efforts were focused on the ways to accelerate water penetration by improving capillary action.

D. Effect of Ethanol Dehydration or Freeze-drying on Swelling and Elastic Properties of Superporous Hydrogels Sample #2 took more than 30 minutes for equilibrium swelling. This rather slow swelling originated from the drying process. The synthesized superporous hydrogel contained water which was present in the monomer mixture (the concentration of monomer was 17.4% (w/v)). During the drying process, the individual polymer chains were brought together due to the high surface tension of water (72 dyn/cm at room temperature), and this action closed some of the pores. As a result, the foam shrank to a smaller and more condensed piece (density of 0.76 g/cm$^3$). Many of the capillary channels were closed or partially blocked to form "dead end" structures. Thus, no capillary action is expected even in contact with water. It was found that ethanol dehydration was a good approach to solve the problem associated with the air drying process.

In Sample #4, in Table 2, the synthesized superporous hydrogels were dehydrated using absolute ethanol. After a superporous hydrogel was synthesized in a test tube, 5–10 ml of absolute ethanol was added to the test tube to dehydrate the superporous hydrogel. After the initial dehydration step (during which some water was replaced by ethanol), the superporous hydrogel was retrieved and further dehydrated in a plate containing 50 ml of absolute ethanol several times to ensure replacement of all the water by ethanol.) During the dehydration process, the soft and flexible superporous hydrogels became hard and brittle. After the dehydration was completed, the excess ethanol in dehydrated superporous hydrogels was removed by draining using a paper towel. Then the superporous hydrogels were dried in a 55° C. oven for a day. For Sample #5, the synthesized superporous hydrogels were first allowed to swell to equilibrium in DDW before being dehydrated using absolute ethanol.

The ethanol-dried superporous hydrogels without preswelling in DDW (Sample #4) had a density of 0.26 g/cm$^3$, which is much lower than that of Sample #2 (0.76 g/cm$^3$). This means that the ethanol dehydrated superporous hydrogels had much higher porosity. The swelling ratio of Sample #4 was similar to that of Sample #2, indicating that dehydration did not change the water absorbency. The swelling time, however, was greatly decreased in Sample #4 (4.8 min in Sample #4 vs. 31 min in Sample #2).

The major factor that contributes to the fast swelling of ethanol dehydrated superporous hydrogel is the preserved capillary channels. Because ethanol is a non-solvent to the polymer, during the dehydration process, water was replaced by ethanol, and consequently the polymer chains were precipitated from the ethanol and lost their flexibility. This is why the superporous hydrogels became hardened after the dehydration. When the dehydrated superporous hydrogels were dried in 55° C. oven, because the polymer chains could not move freely, they could not be brought together by the low surface tension of ethanol. Therefore, the superporous hydrogels did not collapse and thus the capillary channels were preserved after the drying process. Ethanol has a low surface tension (22 dyn/cm compared with 72 dyn/cm of water at room temperature), which means the driving force for the collapse of the polymer network is smaller. For the dehydration process, not only ethanol, but other conventional organic solvents such as acetone, methanol, and isopropanol, etc., can also be used.

Superporous hydrogels dehydrated by ethanol had a larger pore size and lower density than those without ethanol dehydration. SEM pictures showed that the number and the size of pores of Sample #4 were much greater than those of Sample #2. Also the pores in Sample #4 were interconnected to form capillary channels so that water could easily penetrate to the center of the superporous hydrogels. Similar structural differences can also be found in sucrose superporous hydrogels prepared with and without ethanol dehydration.

In Sample #5, the superporous hydrogels were swollen in DDW before dehydration with ethanol. Superporous hydrogels of Sample #5 had a density of 0.13 g/cm$^3$, which is even lower than 0.26 g/cm$^3$ of Sample #4. This is because in Sample #5, the superporous hydrogels were fully swollen before the dehydration, i.e., polymer chains were fully relaxed. Dehydration under this state resulted in a superporous hydrogel with larger volume. Lower density in Sample #5 suggested that they had an even better capillary system. This contributed to the slightly faster swelling time in Sample #5 (4.1 min) than Sample #4 (4.8 min).

In plastic foams, such as a phenolic foam, the most common type of pores are several hundred micrometers in diameter. In addition to those large pores (which were called macrocells), there are secondary pores with diameters about 1 $\mu$m (which were called microcells) in the wall of the macrocells [Shutov, F. A., 1991]. Microcells were also found in the present superporous hydrogels. The microcells were 0.1 to 5 microns in size as measured by SEM. The microcells were 2–3 orders of magnitude smaller than the main pores of the superporous hydrogels.

All of the superporous hydrogel samples were also freeze-dried. The freeze-dried superporous hydrogels exhibited unique properties that have not been observed before. The swelling properties (i.e., swelling ratio and swelling time) of the freeze-dried superporous hydrogels were improved (i.e., they swell faster to a larger size) compared to the ethanol-dehydrated superporous hydrogel samples. The most unique property of the freeze-dried superporous hydrogels was their elasticity. Unlike air-drying or ethanol-drying, the freeze-drying resulted in solid matrices which were highly flexible. Thus, the freeze-dried superporous hydrogels were compressed, elongated, or changed to any shape without breaking. This elastic property of dried superporous hydrogels is of paramount importance in handling of the dried samples for further manipulation. For example, compressing the dried superporous hydrogels to fit into gelatin capsules for oral administration can easily be done without breaking due to their high flexibility.

E. Effect of Wetting Agent on the Swelling Kinetics of Superporous Hydrogels

The mere presence of interconnected capillary channels is not enough for a good capillary action. The surface of the superporous hydrogels must also have good wettability. Both samples #4 and #5 in Table 2 had good capillary channels, but the water penetration still took more than 4 minutes. The major reason for this was that the surface of superporous hydrogels did not have good wettability. The surface wettability is mainly determined by the type and properties of polymers, the surface roughness, and the swelling medium. Since the surface roughness at the microscopic level is not easy to control, and the most useful medium is water, the surface properties of the superporous hydrogel were changed using different wetting agents.

Wetting agents change the surface wettability. As described in U.S. Pat. No. 5,149,335, Voranol® (a polyol made by Dow Chemical Company) can be used as a wetting agent to increase the swelling rate of polyacrylate hydrogel particles. Sample #6 was made by dehydrating the superporous hydrogels with ethanol containing 1% Voranol$_{240-800}$® (the numbers indicated for Voranol are related to the hydroxy number and the molecular weight). As shown in Table 2, Sample #6 treated with Voranol had the similar density and swelling ratio to those of Sample #4. However, Sample #6 had a faster swelling time (t=2.8 min) than Sample #4 (t=4.8 min). This showed that the wetting agent could decrease the swelling time by providing better surface wettability. It is possible that other wetting agents can decrease the swelling time even more.

F. Effect of Moisture Content on the Swelling Kinetics of Superporous Hydrogels

Samples #7 and #8 in Table 2 were prepared by moistening Sample #2 and 4, respectively. A dried superporous hydrogel was placed on a support which was placed in a covered container with a small amount of water at the bottom. This device constituted a moisture chamber. Sample #7 was made by placing Sample #2 in the moisture chamber for 24 h at room temperature. The superporous hydrogel absorbed 126±11% of its original weight moisture. Sample #8 was made by placing Sample #4 in the moisture chamber for 12 h at room temperature. It absorbed 81±4% of its original weight moisture. The amount of moisture absorbed was controlled by the length and the temperature of moistening.

The swelling ratio did not change after moisturization. All four samples (Sample #2, 4, 7, 8) had similar swelling ratios in DDW (Table 2). However, moistening significantly decreased the swelling time. After this treatment, the swelling time of Sample #7 decreased from 31 minutes (Sample #2) to only 7 minutes, while the swelling time of Sample #8 decreased from 4.8 minutes (Sample #4) to only 37 seconds. As previously mentioned, water penetration is the time-limiting step for the swelling of superporous hydrogels. The decreased swelling time after moistening is thought to be due to improved surface wettability of the superporous hydrogels.

The change of surface wettability after moistening is caused by the amphiphilic property of the hydrogels. The polymer chains in the hydrated state had high mobility. When a superporous hydrogel was dried, the polymer chains at the air-polymer interface changed their orientation and/or conformation to decrease the free energy so that the relatively hydrophobic side chains or backbones faced the air. This led to the change of surface character from relatively hydrophilic to relatively hydrophobic. During the moistening treatment, this process reversed. The polymer chains changed their orientation and/or conformation again and the surface character became relatively hydrophilic [Holly, F. J. et al, 1976; Ratner, B. D. et al., 1986]. This change caused the improved wettability in Sample #7 and 8.

G. Effect of Superdisintegrants on the Swelling Kinetics of Superporous Hydrogels Ethanol dehydration of superporous hydrogels significantly decreases the swelling time. This process, however, requires repetitive use of ethanol to complete dehydration. In an attempt to find a simpler approach, it was attempted to incorporate a "superdisintegrant" into the superporous hydrogels.

Superdisintegrants, such as Ac-Di-Sol®, Primojel®, Explotab®, and Crospovidone® have been used extensively in tablets and capsules to promote their fast disintegration. The mechanism of disintegration is based on swelling, wicking, and deformation of the disintegrants [Kanig, J. L. et al., 1984]. When a compressed tablet is placed in aqueous solution, water can be quickly absorbed, and the swelling of the disintegrant breaks apart tablets quickly.

As mentioned above, air-dried superporous hydrogels lost the interconnected capillary channels (Sample #2 in Table 2). In the presence of incorporated superdisintegrants, however, "dead-ended" structures in the collapsed superporous hydrogels can be expanded by the swelling of the incorporated superdisintegrant and the collapsed channels can be opened up to recover capillary action.

1. Effect of Crosslinked Sodium Carboxymethylcellulose (Ac-Di-Sol®)

Ac-Di-Sol® (FMC Corporation) is a crosslinked sodium carboxymethylcellulose. In the dry state, it exists as stiff fibers with diameter of 10–20 $\mu$m and length of 100–200 $\mu$m. To be incorporated in Samples #9–12 in Table 2, various amounts (50 mg–200 mg) of Ac-Di-Sol® were added to the monomer solution before the addition of TEMED. The solution was stirred using a spatula to evenly distribute Ac-Di-Sol® so that a viscous mixture was formed. The stirring after the addition of $NaHCO_3$ further mixed Ac-Di-Sol®, and after the beginning of polymerization by addition of $NaHCO_3$, the viscosity increased quickly and the sedimentation of Ac-Di-Sol® to the bottom of the tube was negligible. After the polymerization was complete, the superporous hydrogels were dried in a 55° C. oven for a day.

Samples #9, #10, #11, and #12 in Table 2 had densities of 0.48, 0.39, 0.33, and 0.28 $g/cm^3$, respectively. The increase in the Ac-Di-Sol® content decreased the density of the synthesized superporous hydrogels. When Ac-Di-Sol® was mixed with the monomer solution, it swelled so that monomers (AM and AA) and crosslinker (BIS) were absorbed into the cellulose network. After polymerization is complete, the cellulose network of Ac-Di-Sol® particulates and the crosslinked poly(AA-co-AM) network formed an interpenetrating polymer network (IPN). This IPN formation is limited to the Ac-Di-Sol® particulate, and thus the localized IPNs (or Ac-Di-Sol® particulate) basically function as a crosslinker of the synthesized superporous hydrogels. During the drying process, the rigid Ac-Di-Sol® fibers maintained the network structure so that the superporous hydrogels shrank less. The superporous hydrogels with higher Ac-Di-Sol® content had higher porosity and better capillary channels.

The addition of Ac-Di-Sol®, however, decreased the swelling ratio of the superporous hydrogels. The swelling ratios of Sample #2, 9, 10, 11, and 12 were 328, 294, 192, 120, and 91, respectively. The decrease was due to the increase in crosslinking by the localized IPNs. On the other hand, the addition of Ac-Di-Sol® dramatically decreased the swelling time. The swelling times of Sample #2, 9, 10, 11, and 12 were 31 min, 8.5 min, 1.2 min, 35 sec, and 22 sec, respectively.

The function of Ac-Di-Sol® in promoting the swelling speed was two-fold. First, it helped retain the capillary channels. This is evident from the lower density of superporous hydrogels incorporated with Ac-Di-Sol®. However, when compared with Samples #4, #5, and #6, Sample #12 had higher density but shorter swelling time. This suggested that retained capillary channels were not the only reason for its fast swelling. It is thought that another contribution of Ac-Di-Sol® is its hydrophilicity. Ac-Di-Sol® has high wettability with a contact angle of 0° [Gissinger, D. et al., 1980]. Thus, incorporation of Ac-Di-Sol® made the surface of superporous hydrogels more hydrophilic and with better wettability.

Compared with the ethanol dehydration process, the addition of superdisintegrants is simpler and less expensive. In addition, it has another advantage. After the addition of Ac-Di-Sol®, the monomer solution became viscous. This is good for foam preparation because at higher viscosities, foams can be stabilized longer.

2. Effect of crosslinked sodium starch glycolate (Primolel®)

The effect of Primojel® on the swelling time of superporous hydrogels was also studied. Primojel® is a crosslinked sodium starch glycolate.

Superporous hydrogel containing Primojel® was prepared based on Example 13. The superporous hydrogel was dried in a 55° C. oven after the synthesis. For comparison, control superporous hydrogels containing no Primojel® were also prepared. They were either dried in a 55° C. oven after synthesis or were dehydrated by ethanol followed by oven drying. The swelling time of these three groups of superporous hydrogels were tested in DDW. The swelling time of the superporous hydrogel containing no Primojel® and without ethanol dehydration was 8.5 min. The swelling time of superporous hydrogel containing no Primojel® but with ethanol dehydration was 1.4 min. The swelling time of superporous hydrogel containing 100 mg Primojel® but without ethanol dehydration was only 0.6 min. This study shows that Primojel® can also significantly decrease the swelling time of a superporous hydrogel.

In addition to Ac-Di-Sol® and Primojel®, other tablet disintegrants such as Explotab® and Crospovidone® have a similar mechanism in tablet disintegration. As with Ac-Di-Sol®, Primojel® and Explotab® are very hydrophilic with a contact angle of 0° [Gissinger, D. et al., 1980]. They are also expected to have the ability to promote the swelling of superporous hydrogels.

H. Effect of Crosslinking Density on the Swelling Kinetics of Superporous Hydrogels To study the effect of crosslinking density on the swelling properties, superporous hydrogels containing different amount of crosslinker were prepared. The crosslinker (BIS) contents in Sample #2, #13, and #14 in Table 2 were 0.3 mol %, 0.6 mol %, and 0.9 mol % of the monomer content, respectively.

Table 2 shows that the increase in the crosslinker concentration decreased the density of the superporous hydrogels (0.76, 0.45, and 0.38 g/cm$^3$ for Sample #2, #13, and #14, respectively). It is not surprising that the swelling ratio also decreased when more crosslinker was incorporated. It is interesting to note that when more crosslinker was used, the swelling time also decreased significantly (31 min, 13.4 min, and 3.1 minutes for Sample #2, #13, and #14, respectively). The faster swelling of Sample #13 and #14 is explained based on their structure observed by SEM. At higher crosslinking density, the polymer networks became more rigid. Therefore, during the drying process, the superporous hydrogels shrank less and the capillary channels were less likely blocked. The interconnected capillary channels were observed in Sample #14 while many of these channels were blocked in Sample #2.

I. Other Factors Affecting the Swelling Kinetics of Superporous Hydrogels

The type of polymer can have great impact on the swelling kinetics of superporous hydrogels. For superporous hydrogels having the same porous structures, ones with better wettability swell faster. It is believed that the main factor determining water wettability of a hydrogel is the chemical structure of the polymer network at the interface [Holly, F. J. et al., 1976]. Superporous hydrogels synthesized from glycidyl acrylate modified sucrose monomer swelled to equilibrium in less than 0.3 minute after being treated by ethanol dehydration [Cehn, J., 1997] while similar size superporous hydrogels prepared by the same method (Sample #4) took 4.8 minutes to reach equilibrium. This difference is partially attributed to the different wettability of the polymers.

The porosity can also affect the swelling kinetics of superporous hydrogels. The porosity of superporous hydrogel is mainly determined by the amount of blowing agent added. Superporous hydrogels with higher porosity are less likely to have blocked channels. In addition, when more blowing agent is used, the superporous hydrogels have thinner cell walls which results in a shorter characteristic time $t_2$. Superporous hydrogels prepared with more acid had faster swelling time than those prepared with less acid.

It has been suggested that the wettability of polymeric foams can be improved by washing with Span® 20 solution or CaCl$_2$ solution [DesMarais, T. A. et al., 1994]. In this study, superporous hydrogels were treated by the same processes. Such treatments, however, did not result in any improvement on the swelling kinetics of the superporous hydrogels.

III. Mechanical Properties of Superporous Hydrogels and Superporous Hydrogel Composites The high mechanical strength of superporous hydrogels is important for many applications. Quite often the mechanical strength of superporous hydrogels, as well as conventional hydrogels, is low to compromise the usefulness of other functional properties of hydrogels and superporous hydrogels. One of the important applications of hydrogels and superporous hydrogels is in the development of oral controlled drug delivery systems. Hydrogels have been used as a platform for long-term (more than 24 h) oral drug delivery. Due to the large size and slippery surface of fully swollen hydrogels, they have been successfully used as a gastric retentive device for long-term oral drug delivery [Shalaby, W. S. W., et al., 1992A; Shalaby, W. S. W., et al., 1992B]. One of the limitations of using a hydrogel-based gastric retentive device is that the dried hydrogels swelled too slow so that all the dried hydrogels administered to dogs were emptied into the stomach before fully swelling to a desired size. To avoid the slow swelling problem with conventional hydrogels, superporous hydrogels were synthesized as mentioned above. While the superporous hydrogels swelled very quickly regardless of size, the mechanical strength of fully swollen superporous hydrogels was poor. Therefore, various superporous hydrogel composites were made to enhance the mechanical strength of the fully swollen superporous hydrogels.

During the study on the swelling kinetics of various superporous hydrogels described above, it was observed that some samples of superporous hydrogels containing Ac-Di-Sol® or Primojel® maintained high mechanical strength even after equilibrium swelling. This led us to investigate further the mechanical properties of superporous hydrogel "composites", i.e., superporous hydrogels prepared with a disintegrant. Formulation variables, such as the amount of crosslinker, amount of disintegrant, type and amount of plasticizer, type of monomer, amount of blowing agent, as well as process variables such as acidification, all affect the mechanical properties of the superporous hydrogels.

A. Testing Method of Mechanical Properties

A bench comparator (B.C. mes Company, Waltham, Mass.) was used to test the mechanical properties of the superporous hydrogels. A superporous hydrogel that was swollen in simulated gastric fluid (SGF) was placed longitudinally under the lower touch of the bench comparator that was connected to a micrometer gauge.

The superporous hydrogel was supported by a lab jack. Weights were applied to the upper touch of the bench comparator in increasing amounts. The swelling height of the superporous hydrogel under pressure was read from the gauge. The pressure applied to the superporous hydrogel was calculated from the amount of weights and the contact area of the lower touch. Two parameters, swelling height under 100 cm water pressure and ultimate compression pressure (UCP), were determined to characterize the mechanical properties of the superporous hydrogels. The UCP was determined by applying increasing amounts of weights until a point when the superporous hydrogel started cracking. The pressure at that point was defined as the UCP.

B. Effect of Ac-Di-Sol® on the Mechanical Properties of Superporous Hydrogels

The presence of a disintegrant, such as Ac-Di-Sol®, in superporous hydrogels is critical for the improved properties of the superporous hydrogels. As discussed above, Ac-Di-Sol® significantly improved both the swelling kinetics and the mechanical properties of superporous hydrogels. In another study, Ac-Di-Sol® was also found to significantly increase the mechanical strength of conventional, non-porous hydrogels. The effect of Ac-Di-Sol® on the mechanical strength of superporous hydrogels was examined in more detail.

Superporous hydrogels containing different amounts of Ac-Di-Sol® (0 to 300 mg) were prepared based on poly (AM-co-SPAK) (see Example 10) except that none of these superporous hydrogels were acidified, i.e., they were not treated with simulated gastric fluid. The mechanical properties of these superporous hydrogels were studied on the bench comparator after they swelled to the equilibrium size in SGF.

Figure 2:
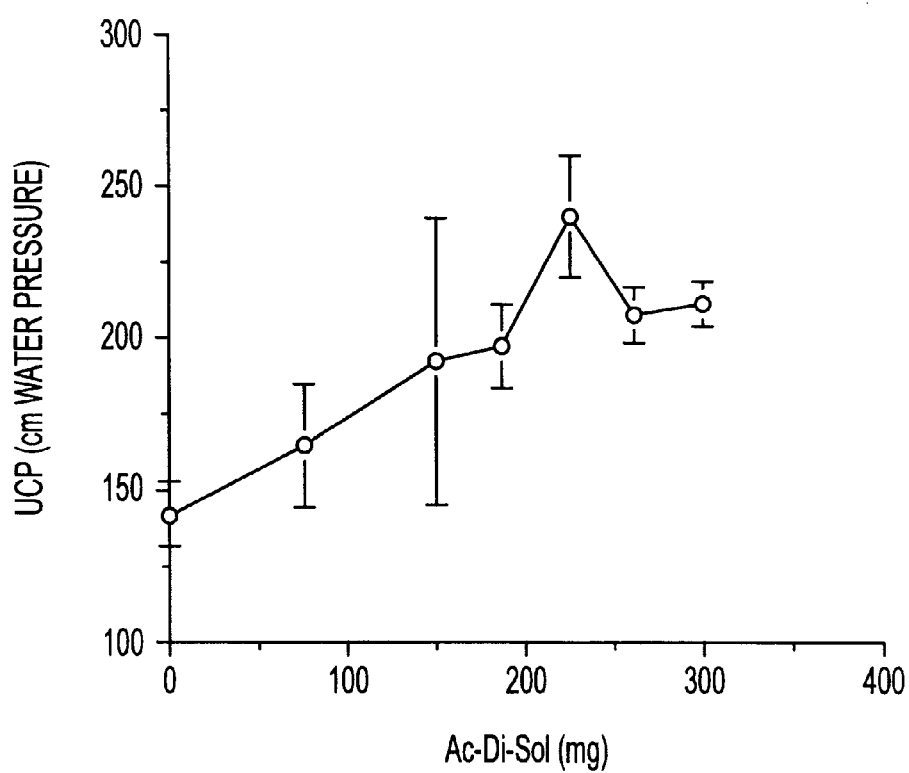
FIG. 2 depicts the effect of Ac-Di-Sol® on the mechanical properties of superporous hydrogel composites as represented by the ultimate compression pressure (UCP).

Incorporation of Ac-Di-Sol® slightly decreases the swelling size of the superporous hydrogels from 1.8 to 1.2 cm in the presence of 100 cm water pressure. On the other hand, it considerably increases the UCP value (o in FIG. 2) of the superporous hydrogels from below 150 to about 250 cm water pressure. This is a rather dramatic increase in mechanical strength. It is thought that the addition of Ac-Di-Sol® increases the effective cross-linking density of the superporous hydrogel. Ac-Di-Sol® is also thought to function as a filler in the superporous hydrogel. The increase in effective crosslinking density by physical entanglement is different from increasing the crosslinking density by other conventional crosslinkers such as BIS. When the concentration of Ac-Di-Sol® was too high, the viscosity of the monomer solution became too high, and this made a good mixing of all the ingredients difficult. A good mixing was achieved when up to 270 mg Ac-Di-Sol® was added.

Figure 3:
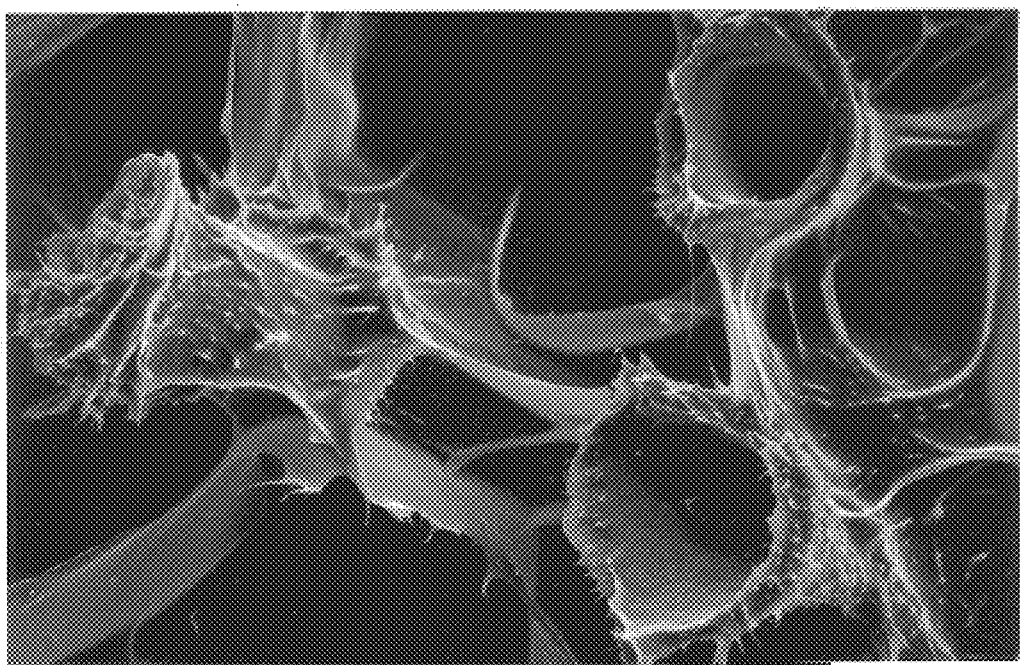
FIG. 3 is an SEM photograph of a freeze-dried hydrogel composite containing Ac-Di-Sol® fibers, wherein the Ac-Di-Sol® fibers are bonded to the polymer matrix of the hydrogel via locally interpenetrating networks (IPNs). The hollow lumen structure of the superporous hydrogel composite, which facilitates capillary action, is clearly exhibited.

When Ac-Di-Sol® fibers were mixed with the monomer solution, they swelled and absorbed the monomer solution. When the polymerization was initiated, the monomers inside the Ac-Di-Sol® fibers polymerized along with the bulk monomer solution so that local interpenetrating polymer networks (IPNs) around the Ac-Di-Sol® fibers were formed. Ac-Di-Sol® fibers were chemically bonded to the superporous hydrogel matrix as an integral unit. This structure allows significant increase in the overall mechanical strength of superporous hydrogels. The physical entanglements of Ac-Di-Sol® fibers with the polymer network is also confirmed by SEM (FIG. 3).

C. Effect of Type of Monomer on the Mechanical Properties of Superporous Hydrogels The type of monomer used in the superporous hydrogel preparation significantly affects the mechanical properties of the superporous hydrogels. When acrylamide (AM) was used as the only monomer, the superporous hydrogels did not show large swelling volume nor good mechanical strength. When SPAK was used alone, the superporous hydrogels swelled to a large size but were not strong. When AM and AA were copolymerized, the superporous hydrogels did not swell very large in SGF, and also the superporous hydrogels deformed to a very small size under 100 cm water pressure. However, when AM and SPAK were copolymerized, the superporous hydrogels showed good swelling and also good mechanical properties.

D. Effect of Acidification on Mechanical Properties of Superporous Hydrogels

Various post-treatments of synthesized superporous hydrogels were attempted to improve the mechanical strength of superporous hydrogels. After the superporous hydrogels were prepared as in Example 10, they were washed in the SGF (pH 1.2) for 24 h. They were then dried in a 60° C. oven or air dried at room temperature. The dried superporous hydrogels were allowed to swell in SGF and their mechanical properties were tested using the bench comparator.

Superporous hydrogels with three different post-treatments were tested: (A) superporous hydrogels without washing in SGF; (B) superporous hydrogels washed in SGF and then oven dried at 60° C. for 24 h; and (C) superporous hydrogels washed in SGF and then air dried at room temperature for 5 days. The washing step partially acidified the anionic $SO_3^-$ group into $SO_3H$ group, and it substantially changed the properties of the superporous hydrogels. The UCP value for the three samples A, B, and C were 189, 284, and 368 cm water pressure, respectively. The acidification of the superporous hydrogels made them much stronger than the superporous hydrogels without acidification. Moreover, the UCP of the acidified superporous hydrogels that were dried at room temperature were even stronger than those dried in a 60° C. oven. It is clear that acidification provided a significant improvement in the mechanical properties of superporous hydrogels.

IV. Mechanical Properties of Hydrogel Composites

Highly swelling hydrogels usually possess weak mechanical strength and such a property limits applications of otherwise useful hydrogels. Thus, improving the mechanical properties while maintaining high swelling ratio is highly desirable even for conventional hydrogels. Since the finding that Ac-Di-Sol® fibers increased the mechanical strength of superporous hydrogels, the effect of Ac-Di-Sol® fibers on the mechanical strength of conventional hydrogels was examined. It was found that when Ac-Di-Sol® fibers were used to make conventional hydrogel composites, the increase in the mechanical strength was even more significant than for the superporous hydrogels.

A. Synthesis of Hydrogel Composites

In a plastic test tube (17 mm×100 mm), Ac-Di-Sol®, AM, BIS, APS, and distilled water were sequentially added to make the final volume of 5 ml. The amount of Ac-Di-Sol® was varied as listed in Table 3. The final AM concentration was 10% (w/v), and the concentration of BIS (crosslinker) was 0.46 mol % of the monomer. The concentration of APS was 4% (w/w) of the monomer, AM. The solution was then stirred to thoroughly mix all the ingredients. Then, TEMED, at the concentration of 4% (w/w) of the monomer, was added and the solution was stirred vigorously for 15 seconds for further mixing. The gelling started within 30–60 seconds after the addition of TEMED. The prepared hydrogels were cured at room temperature for 24 h followed by washing in distilled water for 4 days. Polyacrylamide (PAM) hydrogels containing Crospovidone® XL were also synthesized in the same manner (Table 3). The contents of Ac-Di-Sol® and Crospovidone® XL in the dried hydrogels were calculated based on the amount added. As a control, PAM hydrogels containing no disintegrant but with different amounts of crosslinking agent were synthesized. The final monomer concentration was also 10% (w/v) for all samples, and the concentration of BIS was varied from 0.46 mol % to 1.84 mol % of the monomer.

B. Characterization of Hydrogel Composites

Fully swollen hydrogels were cut into discs with 1 cm length. Their diameter ranged from 1.2 cm to 1.8 cm. The mechanical properties were tested using a bench comparator. Briefly, a cylindrical, swollen hydrogel was placed under a plate which was connected to a micrometer gauge. Weights were applied in increasing amounts and the hydrogel deformation (i.e., the height difference between undeformed and deformed hydrogel) was recorded for each weight. After each measurement, the weights were completely removed and the hydrogel was allowed to recover to its initial height before the next weight was added. The linear portion of the force vs. deformation graph which occurred when the deformation was less than 10% of its original height was used to calculate the force/deformation coefficient. The compression modulus was calculated by the following equations:

$$E_c = SH_s/A_s$$

where $E_c$ is compression modulus, S is force/deformation coefficient. $H_s$ is the height of the fully swollen gel, $A_s$ is the area of the top of a fully swollen gel.

The washed hydrogels were air dried to a constant weight. The swelling study was conducted in distilled water at room temperature. At timed intervals, the gels were removed from water, blotted to remove excess water, and weighed. The swelling ratio Q was calculated by:

$$Q = (W_s - W_d)/W_d$$

where $W_s$ and $W_d$ were the weights of the swollen and dried gels, respectively.

Figure 4A:
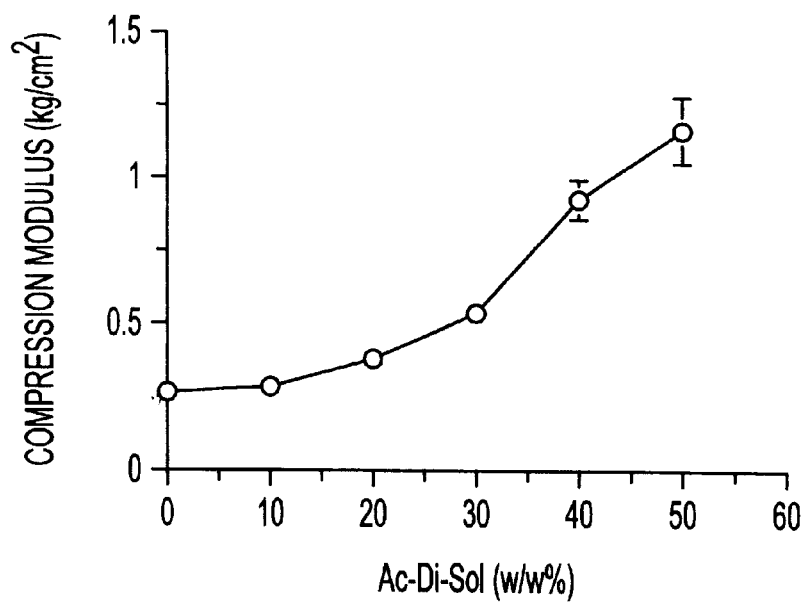
FIG. 4 depicts the effect of Ac-Di-Sol® on the compression modulus (A) and swelling ratio (B) of polyacrylamide hydrogel composite with the amount of Ac-Di-Sol® expressed as a percent of the total weight of dried hydrogel.
Figure 4B:
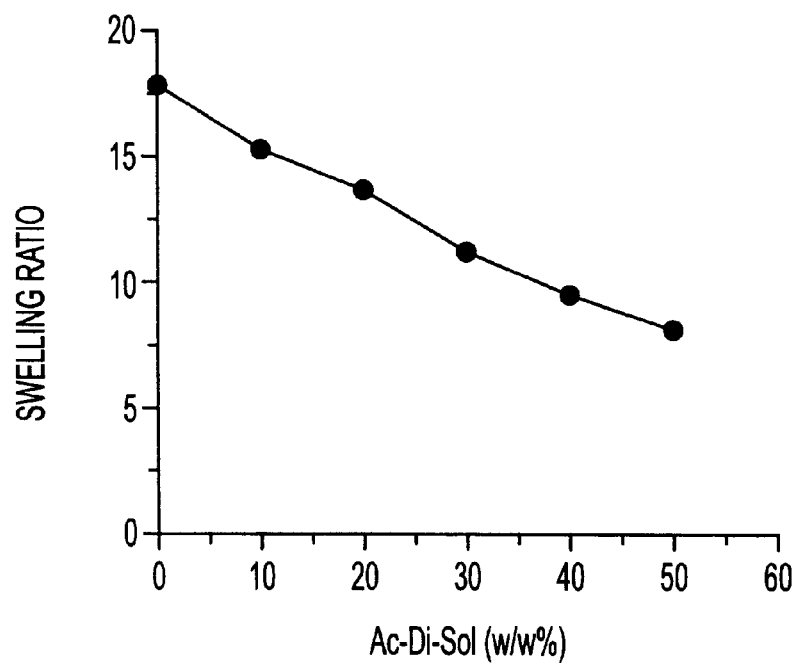

FIG. 4 shows changes in the swelling ratio and compression modulus of the polyacrylamide and Ac-Di-Sol® composites as a function of the Ac-Di-Sol® content. When the Ac-Di-Sol® content increased from 0% to 50% of the total weight of the dried hydrogel, the compression modulus (representing the resistance to pressure) increased 4.7 fold from 0.25 to 1.17 kg/cm$^2$ (FIG. 4-A) and the swelling ratio decreased 2.4 fold almost linearly from 19.0 to 7.8 (FIG. 4-B). The decrease in the equilibrium swelling ratio is understandable since the individual Ac-Di-Sol® fibers are expected to function as physical crosslinking agents.

The changes in the swelling ratio and compression modulus with increase in the Crospovidone® XL content were similar to those for the polyacrylamide and Ac-Di-Sol® composites described above. When the content of Crospovidone® XL increased from 0% to 60% of the hydrogel dry weight, the compression modulus increased from 0.25 to 1.07 kg/cm$^2$ (4.2 fold), while the swelling ratio decreased from 19.0 to 4.3 (4.4 fold).

For conventional hydrogels using an increasing amount of crosslinker such as BIS but containing no Ac-Di-Sol® or Crospovidone® XL, the increase in the compression modulus was small. When the BIS content increased from 0.46 mol % to 1.84 mol %, the compression modulus increased from 0.25 to 0.71 kg/cm$^2$ (2.8 times), and the swelling ratio decreased from 19.0 to 9.2 (2.1 fold). The effect of BIS in increasing the compression modulus showed a limit. After the BIS content reached 1.4 mol %, the compression modulus curve started to level off. More crosslinker did not further increase the compression modulus. However, by using more Ac-Di-Sol® or Crospovidone®, much stronger hydrogels could be made. Increasing the concentration of BIS alone could not make the hydrogels as strong as the Ac-Di-Sol® or Crospovidone® reinforced hydrogel composites. Between Ac-Di-Sol® and Crospovidone® XL, Ac-Di-Sol® was a better choice in making the hydrogel composites.

In addition to the above-mentioned materials, other fibers can also be used to improve the mechanical properties of hydrogel composites. It was found that when short cotton fibers (1–4 mm) were incorporated in polyacrylamide hydrogels, the compression modulus was significantly increased.

V. Gastric Retention of Superporous Hydrogels and Superporous Hydrogel Composites The importance of controlled drug delivery systems that release active ingredients over an extended period of time has long been recognized in pharmaceutical research. It provides great convenience to the patients and improves the therapeutic efficacy by maintaining a consistent and uniform blood level of medication over an extended period of time. of the many routes of drug delivery, oral administration remains the most convenient and commonly employed means of introducing drugs to the systemic circulation. The duration of oral controlled drug delivery is limited by the time that the oral dosage forms remain in the upper small intestine. All of the oral dosage forms without suitable platforms are emptied from the stomach in an hour or so and pass through the upper small intestine in less than a few hours. Since most drugs are absorbed only from the upper small intestine, they have to be administered a few times a day, unless the drug has a long half-life.

Gastric retention devices are designed to prolong the retention time of a dosage form in the stomach to realize long-term oral drug delivery. A hydrogel platform was used for oral drug delivery for up to 50 hours after a single administration [Shalaby, W. S. W, et al., 1992A]. In those studies, however, the hydrogel dosage form had to be preswollen to prevent premature emptying of the dosage form from the stomach due to the slow swelling to a desired size. The use of superporous hydrogels and their composites solve the problems associated with slow swelling and the weak mechanical strength.

The gastric retention of superporous hydrogels is based on their fast swelling property. The concept of gastric retention is illustrated in FIG. 5. A superporous hydrogel or its composite is encapsulated in a capsule so that the initial volume is small enough for easy swallowing (FIG. 5-A). After oral administration, it swells quickly (in less than 10 minutes including the dissolution of the gelatin capsule) in the gastric juice to a large size so that its emptying into the intestine is prevented (FIG. 5-B). The superporous hydrogel or its composite may contain drugs for controlled release. The superporous hydrogel or its composite can be slowly degraded in the stomach by either mechanical force, or chemical or enzymatic hydrolysis of the polymer chains constituting the hydrogel (FIG. 5-C). Eventually, the degraded superporous hydrogel or its composite is eliminated from the stomach (FIG. 5-D).

For practical application as a gastric retention device, superporous hydrogels must possess the following properties. First, before swelling, they should be small enough for easy swallowing. In the present study, size 000 hard gelatin capsules were used to house the superporous hydrogels and their composites. Second, they also have to swell fast to prevent premature emptying into the intestine. It was found that complete swelling in less than 10 minutes was adequate to prevent premature emptying. Third, the size of the swollen superporous hydrogels or their composites have to be big enough to be retained in the stomach. The diameter of the pyloric sphincter is about 2 cm in humans. Under normal conditions, the pyloric sphincter is closed. However, it can be stretched and pass an object even larger than 2 cm. Finally, the fully swollen superporous hydrogels or their composites have to be strong enough to withstand peristaltic contraction by the gastric tissues (B-1B→5 in FIG. 5).

In an in vivo gastric retention experiment, radiopaque markers were used to locate the exact position of superporous hydrogels or their composites in the gastrointestinal tract. Small hydrogel pellets containing $BaSO_4$ were used as the X-ray marker. The $BaSO_4$-containing hydrogel pellets were prepared in a thin plastic tube (inner diameter of 3.35 mm). The following components were sequentially mixed in a glass vial: 1300 $\mu$l of 50% AM; 800 $\mu$l of 2.5% BIS; 150 $\mu$l of 20% APS; 1300 $\mu$l of 40% $BaSO_4$ suspension (E-Z-EM, Inc.); and 80 $\mu$l of 20% TEMED. The vial was swirled to mix the ingredients after each component was added. The mixture was then injected into the plastic tube. The gelling of the mixture started within 5 minutes after the addition of TEMED. After curing for 1 h at room temperature, the noodle-like gel was retrieved from the plastic tube, cut into small segments, and dried in a 60° C. oven for 5 h. The dried gel pellets were white and had diameter of 2 mm and length of 2 mm.

To incorporate the $BaSO_4$-containing hydrogel pellets into a superporous hydrogel or its composite, two to six pellets were placed in the monomer solution in Example 10 before adding APS. After the addition of $NaHCO_3$, the mixture was mechanically stirred for 5–10 seconds to evenly distribute the pellets.

$BaSO_4$-containing hydrogel pellets gave the following advantages. They have very high contrast over background and therefore are easy to monitor even after they are swollen for several days. The size of the dried hydrogel pellets is very small so that it does not affect the packing of a superporous hydrogel into a gelatin capsule. Several pellets can be dispersed in a superporous hydrogel so that the fragmentation of the superporous hydrogel can be easily monitored.

The superporous hydrogels that were placed inside gelatin capsules were tested in dogs for gastric retention. Superporous hydrogels with different properties were tested under fasted or fed conditions. The dogs used in all experiments were about 50 pounds. The fasted condition was achieved by keeping a dog from food for 36 h, but the dog had free access to water. The fed condition was achieved by giving a dog 447 g of canned food right before the oral administration of the capsule. In each experiment (fasted state or fed state), the dog was given 300 ml water by stomach tube right before the oral administration of the capsule. Then the capsule containing the superporous hydrogel was swallowed by the dog with no water. X-ray pictures were taken at different time intervals after the administration of the capsule.

In simulated gastric fluid, the superporous hydrogel was 2.4 cm in diameter and 3.5 cm in length. The UCP was 370 cm water pressure. Three $BaSO_4$-containing hydrogel pellets were incorporated in the superporous hydrogel as radiographic markers. The dog was in the fed state in the beginning of the study. The fed state was maintained for 6 h. After that, no food was found in the stomach and the dog was in the fasted state.

Figure 6A:
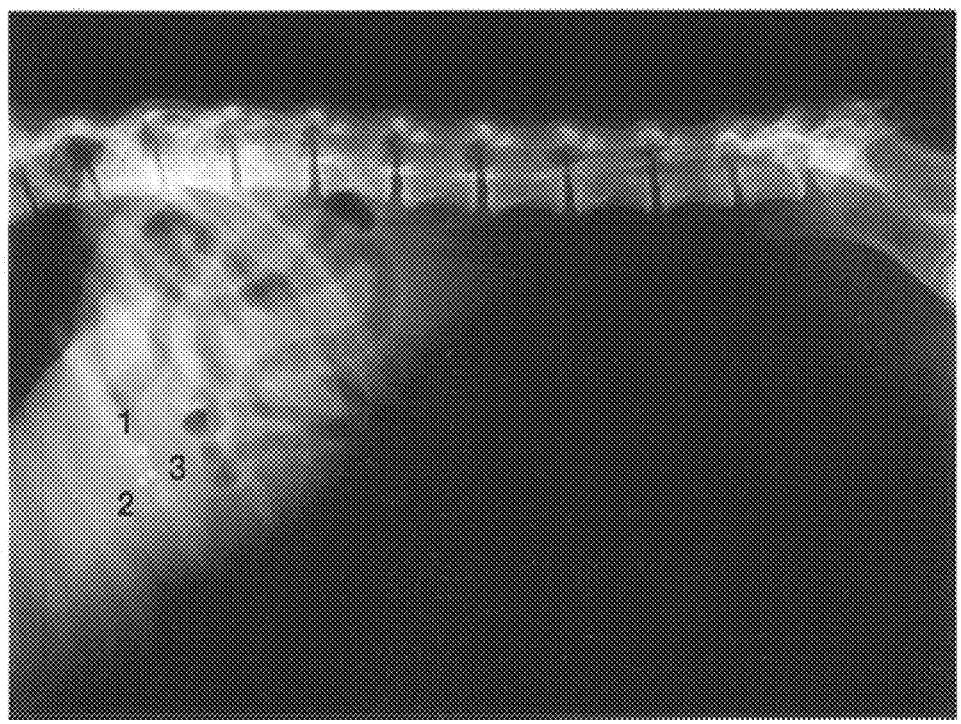
FIGS. 6A and 6B show X-ray photographs of a superporous hydrogel taken 27 hours (A) and 32 hours (B) after administration to a dog. The dog was in the fed state for the first six hours and in the fasted state thereafter. The superporous hydrogel remained intact in the stomach at least for 27 hours as shown by the three hydrogel pellet markers (#1–3). After 32 hours, one marker (#1) emptied into the intestine while the other two markers (#2–3) were still in the stomach.
Figure 6B:
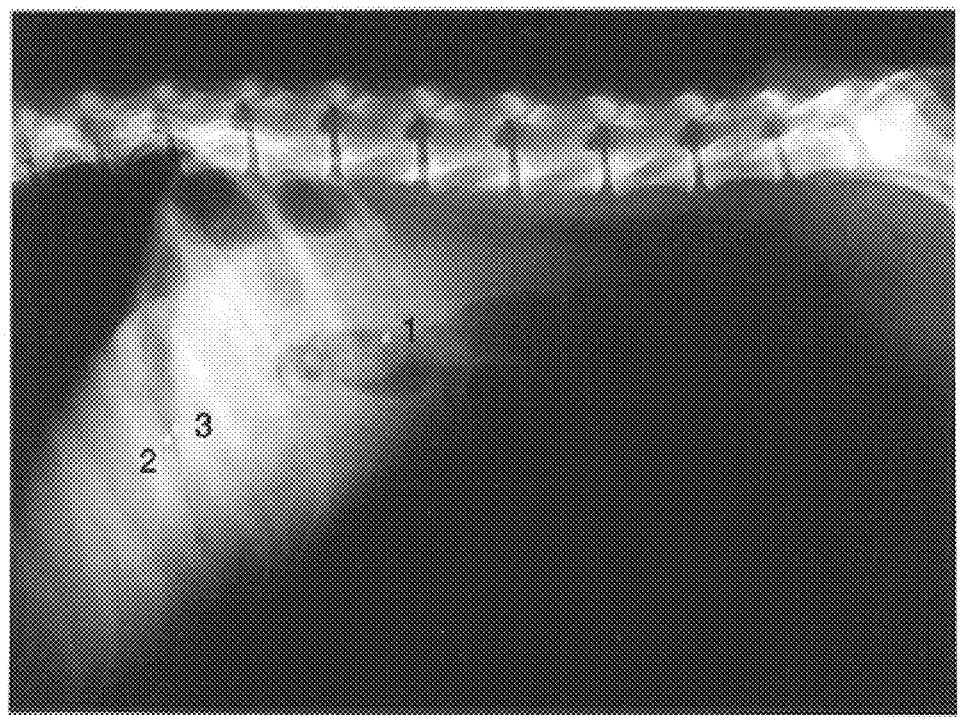

X-ray pictures were taken at time 0, 30 min, 1 h, 2 h, 3 h, 4 h, 5 h, 6 h, 7 h, 8 h, 23 h, 27 h, and 32 h. X-ray images taken at times 27 h and at 32 h are shown in FIG. 6-A and FIG. 6-B, respectively. From time 0 to time 27 h, all three $BaSO_4$-containing hydrogel markers (labeled as 1, 2, and 3) were seen in the superporous hydrogel. These markers maintained their relative positions, indicating that the superporous hydrogel remained intact. The image taken at time 32 h (FIG. 6-B) shows that one of the markers (#1) had gone to the small bowel while the other two (#2 and 3) remained in the stomach. This means that the fragmentation started between times 27 h and 32 h probably due to repetitive gastric contractions. Once the fragmentation starts, the superporous hydrogel is expected to be emptied quickly due to the reduced size.

This experiment clearly shows that improved mechanical strength can prolong the gastric retention time to more than 27 h. The size of the superporous hydrogel in this experiment was large enough to be retained in the stomach, and also the mechanical strength was high enough to withstand the gastric contraction force.

VI. Other Applications

Superporous hydrogels and superporous hydrogel composites can be used in various areas as briefly described below.

Due to the excellent water absorption of superporous hydrogels and superporous hydrogel composites, they are ideal in the improvement of surgical pads for bleeding control and personal hygiene products such as disposable diapers and sanitary napkins. The fast water-absorbing property also allows application of the superporous hydrogels or their composites as a desiccating agent instead of silica gels. Currently, commercially available superabsorbents are in the powder form because particulate gels with only a small size can swell fast. This causes limitations in certain applications [Knack, I. et al., 1991]. The superporous hydrogel and superporous hydrogel composites technique allows preparation of superabsorbent materials in any size and in any shape. Superporous hydrogels are also easy to make and show a number of superior properties to the existing products, especially in their swelling rate. These merits would greatly broaden the applications of superabsorbent polymers. The superporous hydrogels technique can be used to make a wide array of synthetic, semi-synthetic, or natural superporous hydrogels which may replace existing superabsorbents in many applications.

In the controlled drug delivery area, superporous hydrogels and superporous hydrogel composites can be used as a platform for long-term oral drug delivery. Due to the fast swelling and superswelling properties, they can stay in the stomach for a few hours up to more than 24 hours [Chen, J., 1997]. Such a long-term gastric retention time is ideal for long-term oral controlled drug delivery.

In the diet control area, superporous hydrogels and superporous hydrogel composites can be used to control the appetite of healthy people who desire to reduce the volume of food they take. Because of the fast swelling to a very large size, superporous hydrogels and superporous hydrogel composites can remain in the stomach for extended periods of time ranging from hours to days [Shalaby, W. S. W., 1992; Chen, J., 1997]. The presence of bulky superporous hydrogels and superporous hydrogel composites will reduce the space in the stomach and thus the amount of food that can be taken. Thus, they can be used as an alternative therapy for obesity.

In the biomedical area, their unique pore structure provides advantages in making devices for artificial pancreas; artificial cornea; artificial skin; articular cartilage; soft tissue substitutes; cell growth substrates in tissue engineering; burn dressings; surgical augmentation of the female breast; or hemoperfusion in blood detoxification and in the treatment of uremia, among others.

In the biotechnology area, their enormous surface area provides advantages in making materials to be used in the separation of macromolecules and cells from the medium. The presence of extremely large pores makes superporous hydrogels and superporous hydrogel composites ideal materials for chromatographic supports.

The low density of superporous hydrogels and superporous hydrogel composites allows applications as a high-strength, light-weight structural material as well as a packaging material. They will be also good as insulators and fillers in structures with energy-sensitive applications.

Hydrogels which can change their volume rather abruptly upon small changes in environmental conditions are known as "intelligent" or "smart" hydrogels [Park, H. and Park, K.: "Hydrogels in Bioapplications," in Hydrogels and Biodegradable Polymers for Bioapplications, Ottenbrite, R., et al., eds., American Chemical Society, Washington, 1996, pp. 2–10; Park, K. and Park H.: "Smart Hydrogels," in The Polymeric Materials Encyclopedia: Synthesis, Properties and Applications, Joseph C. Salamone, ed., CRC Preess, Boca Raton, Fla., 1996, pp. S200–S206]. Smart hydrogels respond to changes in the environmental conditions, such as temperature, pH, solvent, electric field, specific molecules or ions, light, or pressure. While these smart hydrogels are highly useful in various applications, the typical response time usually ranges from hours to days, and this slow response time sometimes limits the usefulness of the smart hydrogels. By making superporous smart hydrogels, the response time could be reduced to seconds or minutes.

CONCLUSION

The average pore size in superporous hydrogels is several hundred micrometers. The pore size can be controlled very easily using the technique described in this disclosure. One of the advantages of the superporous hydrogels and superporous hydrogel composites described here is that the pore size can be controlled independent of the crosslink density [Anderson, D. M et al., 1991].

To date, numerous hydrogels have been made by changing the composition of monomers to make hydrogels of random copolymers or block copolymers. However, hydrogels containing hydrophilic, particulate composite materials as a crosslinking agent have not been synthesized previously. Hydrogels and superporous hydrogels synthesized in the presence of hydrophilic, particulate composite materials, such as microcrystalline cellulose crystals, crosslinked sodium carboxymethylcellulose (Ac-Di-Sol®), cross-linked sodium starch glycolate (Primojel® and Explotab®), and crosslinked PVP (Crospovidone®), possess unique properties which cannot be obtained otherwise.

One of the important roles of Ac-Di-Sol® is to stabilize the foam during synthesis. Our study has shown that even a small amount of gas bubbles can be retained when Ac-Di-Sol® is added. Ac-Di-Sol® can function as a thickener to prevent gas bubbles from escaping from solution. Thus, when small amounts of blowing agent are used, Ac-Di-Sol® (or other thickener) can help make interconnected channels in superporous hydrogels.

The drying of superporous hydrogels after replacing water with ethanol (or other organic solvents) has a few advantages. Ethanol precipitates polymer chains and thus makes the pores formed by polymer chains less prone to collapse. This results in maintaining of open capillaries even after drying. Thus, swelling of superporous hydrogels dried with ethanol is much faster than control superporous hydrogels dried without ethanol treatment.

While the ethanol drying method results in superporous hydrogels that swell fast from the dried state, use of ethanol is costly compared to simple air drying. The air-dried superporous hydrogel composites maintain the ability to swell fast as for the ethanol dried superporous hydrogels. The air drying of superporous hydrogel composites is an economical way of preparing dried hydrogels that swell fast.

Moistening the dried superporous hydrogels improved the wettability of the capillary channels. Thus, superporous hydrogels or superporous hydrogel composites can be moistened for improving the swelling property. This is because the surface of a hydrated hydrogel is amphiphilic and can become hydrophilic when in contact with a hydrophilic surface, e.g., water, but hydrophobic when in contact with a hydrophobic surface, e.g., air.

By taking advantage of the amphiphilic nature of the hydrogel, we can make fast swelling superporous hydrogels and their composites by freeze-drying the partially moistened superporous hydrogels and their composites. To do this, air-dried superporous hydrogels or their composites can be moistened in a moisture chamber to absorb moisture more than 100% of their original weights. Since only small amounts of moisture are absorbed, the size of the superporous hydrogels or their composites do not change much after this moistening.

After the moistening, the surface of superporous hydrogels or their composites become hydrophilic because the polymer chains on the surface change their orientation to let the hydrophilic groups face the surface. Then these moistened superporous hydrogels or their composites are subject to freeze-drying. When frozen, the polymer chains are expected to lose their mobility and keep the surface hydrophilic. Thus, after freeze-drying, the dried superporous hydrogels or their composites maintain high wetability and swell very fast. This approach is different from freeze-drying of superporous hydrogels and their composites in the fully swollen state. Freeze-drying in the fully swollen state requires a long process time and high energy input to remove the large quantity of water. The above-mentioned approach requires a much shorter freeze-drying time.

While freeze-drying of moistened superporous hydrogels or their composites reduced time and energy for drying, freeze-drying of fully swollen superporous hydrogels provides its unique advantages over others. The most important advantage is the high elasticity. We have found that when fully swollen superporous hydrogels or their composites are freeze-dried, the resulting dry superporous hydrogels and their composites are very elastic. The elasticities of the dried materials are such that the freeze-dried superporous hydrogels and their composites can be stretched, compressed, and changed in shape without breaking. This high elasticity is extremely important in further manipulation of the dried materials for application in various fields including controlled drug delivery and biotechnology.

Fast swelling rate and large swelling size are the most distinctive properties of the superporous hydrogels. Two factors, i.e., wettability and the capillary channels, are most important in affecting the swelling rate of superporous hydrogels. Any factors that promote these two properties will improve the swelling rate of superporous hydrogels.

The air-dried superporous hydrogels do not have good capillary channels due to their collapse during the drying process. Ethanol dehydration can effectively protect the capillary channels and thus greatly improve the swelling kinetics. Voranol® as a wetting agent can improve the wettability of superporous hydrogels and therefore increase the swelling speed. Moistening of the superporous hydrogel surface can also improve the wettability and thus increase the swelling kinetics. Superdisintegrants such as Ac-Di-Sol® and Primojel® increase the swelling kinetics by protecting the capillary channels and improving wettability.

Any polymeric material that can swell more than 20 times of its dry weight in aqueous solution is called a superabsorbent polymer (SAP). High water absorbency and fast swelling kinetics are two of the most desirable properties of SAP. Superporous hydrogels, due to their unique structural properties, can absorb much more water and swell much faster in aqueous solution than conventional non-porous and macroporous hydrogels. For this reason, superporous hydrogels are ideal as superabsorbent materials.

Existing superabsorbents used in baby diapers are made by complicated processes and some involve the use of organic solvents [U.S. Pat. No. 5,149,335]. The use of organic solvent may raise safety and environmental concerns. Currently, all commercially available superabsorbents are in the powder form because particulate gels with only a small size can swell fast. This causes limitations in certain applications [Knack, I. et al., 1991]. The superporous hydrogel technique allows preparation of superabsorbent materials in any size and in any shape. Superporous hydrogels and their composites are also easy to make and show a number of superior properties to existing products, especially in their swelling rate. These merits would greatly broaden the applications of superabsorbent polymers. The superporous hydrogels technique can be used to make a wide array of synthetic, semi-synthetic, or natural superporous hydrogels which may replace existing superabsorbents in certain applications.

The main drawback of superporous hydrogels is that they do not have high mechanical strength. It has been the general observation that porous hydrogels with pore sizes above 40–50 $\mu$m are too weak to maintain the intact structure upon applying force and thus are not suitable to serve as a weight-bearing material [de Groot, J. H. et al., 1990; Kon, M. et al., 1981]. The presence of composite materials in the superporous hydrogels makes them mechanically very strong.

The present invention has been discussed with reference to certain examples for purposes of clarity and understanding. However, it should be appreciated that other obvious modifications and improvements can be practiced according to the principles of the present invention within the scope of the appended claims.

TABLE 2

The dimension, density, swelling ratio, and swelling time of poly(acrylic acid-co-acrylamide) superporous hydrogels and superporous hydrogel composites treated by different processes.

| Sample # | Description | Dimension: diameter (mm) × height (mm) | Density of the dried superporous hydrogel (g/cm$^3$) | Swelling ratio | Swelling time |
|---|---|---|---|---|---|
| 1 | Non-porous hydrogel (control) | 4.8 × 2.3 | 1.30 ± 0.08 | 173 ± 7 | 720 ± 110 min |
| 2 | Superporous hydrogel which was oven-dried after synthesis | 5.8 × 2.8 | 0.76 ± 0.05 | 328 ± 40 | 31 ± 6 min |
| 3 | Superporous hydrogel which was fully swollen in DDW and then oven-dried | 5.8 × 2.7 | 0.80 ± 0.06 | 307 ± 29 | 51 ± 22 min |
| 4 | Superporous hydrogel which was dehydrated by ethanol after synthesis and then oven-dried | 8.0 × 4.0 | 0.26 ± 0.02 | 355 ± 54 | 4.8 ± 1.5 min |
| 5 | Superporous hydrogel which was swollen in DDW, dehydrated by ethanol, and then oven-dried | 10.7 × 5.4 | 0.13 ± 0.02 | 337 ± 76 | 4.1 ± 0.3 min |
| 6 | Superporous hydrogel which was dehyedrated by ethanol (containing 1% Voranol$_{240-800}$ ®) after synthesis, and then oven-dried | 8.1 × 4.0 | 0.25 ± 0.02 | 368 ± 34 | 2.8 ± 0.7 min |
| 7 | Sample #2 absorbed 126 ± 11% (of its original weight) moisture. | 5.9 × 2.9 | 0.76 ± 0.05 | 339 ± 36 | 7 ± 6 min |
| 8 | Sample #4 absorbed 81 ± 4% (of its original weight) moisture. | 8.2 × 4.1 | 0.26 ± 0.02 | 334 ± 10 | 37 ± 3 sec |
| 9 | Superporous hydrogel which was synthesized by adding 50 mg of Ac-Di-Sol ® to the monomer solution and then oven-dried | 6.7 × 3.3 | 0.48 ± 0.05 | 294 ± 44 | 8.5 ± 6.1 min |
| 10 | Superporous hydrogel which was synthesized by adding 100 mg of Ac-Di-Sol ® to the monomer solution and then oven-dried | 7.2 × 3.5 | 0.39 ± 0.02 | 192 ± 18 | 1.2 ± 0.6 min |
| 11 | Superporous hydrogel which was synthesized by adding 150 mg of Ac-Di-Sol ® to the monomer solution and then oven-dried | 7.5 × 3.8 | 0.33 ± 0.04 | 120 ± 23 | 35 ± 9 sec |
| 12 | Superporous hydrogel which was synthesized by adding 200 mg of Ac-Di-Sol ® to the monomer solution and then oven-dried | 7.9 × 4.0 | 0.28 ± 0.01 | 91 ± 22 | 22 ± 4 sec |
| 13 | Bis was 0.6 mol % of monomers (Sample #1~12 contained Bis of 0.3 mol % of monomers). SPH was oven-dried after synthesis. | 6.8 × 3.3 | 0.45 ± 0.04 | 231 ± 12 | 13.4 ± 2.1 min |
| 14 | Bis was 0.9 mol % of monomers. SPH was oven-dried after synthesis. | 7.2 × 3.6 | 0.38 ± 0.03 | 166 ± 26 | 3.1 ± 2.5 min |

TABLE 2-continued

The dimension, density, swelling ratio, and swelling time of poly(acrylic acid-co-acrylamide) superporous hydrogels and superporous hydrogel composites treated by different processes.

| Sample # | Description | Dimension: diameter (mm) × height (mm) | Density of the dried superporous hydrogel (g/cm$^3$) | Swelling ratio | Swelling time |
|---|---|---|---|---|---|

All samples were prepared based on Example 9
No PF127 and NaHCO$_3$ was used in Sample #1.
In Sample #9~12, different amounts of Ac-Di-Sol ® were added.
In Sample #13 and 14, different amounts of Bis were added.
The swelling ratio was tested in deionized destilled water (DDW). The swelling time is the time to reach the equilibrium swelling after a superporous hydrogel or a superporous hydrogel composite is placed in DDW. To measure the swelling time, a superporous hydyogel or a superporous hydrogel composite in disk shape (50 mg to 65 mg in weight) was tested.
At least three samples were tested for each measurement.

TABLE 3

Hydrogel composites made of polyacrylamide and Ac-Di-Sol fibers or Crospovidone XL.

Polyacrylamide - Ac-Di-Sol composites

| Sample | Ac-Di-Sol: AM (w:w) | % weight of Ac-Di-Sol in dried hydrogels | Swelling ratio | Compression modulus E$_c$ (kg/cm$^2$) |
|---|---|---|---|---|
| 1 | 0:100 | 0 | 19.0 | 0.25 |
| 2 | 11:100 | 10 | 15.3 | 0.28 |
| 3 | 25:100 | 20 | 13.6 | 0.38 |
| 4 | 43:100 | 30 | 11.1 | 0.53 |
| 5 | 67:100 | 40 | 9.5 | 0.92 |
| 6 | 100:100 | 50 | 8.0 | 1.17 |

Polyacrylamide - Crospovidone XL composites

| Sample | Crospovidone XL :AM (w/w) | % weight of Crospovidone XL in dried hydrogels | Swelling ratio | Compression modulus E$_c$ (kg/cm$^2$) |
|---|---|---|---|---|
| 7 | 0:100 | 0 | 19.0 | 0.25 |
| 8 | 11:100 | 10 | 14.9 | 0.25 |
| 9 | 25:100 | 20 | 12.3 | 0.25 |
| 10 | 43:100 | 30 | 9.5 | 0.33 |
| 11 | 67:100 | 40 | 7.7 | 0.48 |
| 12 | 100:100 | 50 | 5.9 | 0.64 |
| 13 | 150:100 | 60 | 4.3 | 1.07 |

REFERENCES

1. Wichterle, O. and Lim, D.: Hydrophilic gels for biological use, Nature, 185: 117–118, 1960.
2. Shalaby, W. S. W., Blevins, W. E., and Park, K.: In vitro and in vivo studies of enzyme-digestible hydrogels for oral drug delivery, J. Controlled Rel., 19: 131–144, 1992A.
3. Shalaby, W. S. W., Blevins, W. E., and Park, K.: Use of ultrasound imaging and fluoroscopic imaging to study gastric retention of enzyme-digestible hydrogels, Biomaterials, 13: 289–296, 1992B.
4. Chen, J.: Superporous Hydrogels: Synthesis and Applications, Ph.D. Thesis, Purdue University, West Lafayette, Ind., 1997.
5. Chirila, T. V., Constable, I. J., Crawford, G. J., Vijayasekaran, S., Thompson, D. E., Chen, Y. C., Fletcher, W. A., and Griffin, B. J.: Poly(2-hydroxyethyl methacrylate) sponges as implant materials: In vivo and in vitro evaluation of cellular invasion. [In-vivo and in-vitro evaluation of cellular invasion], Biomaterials, 14: 26–38, 1993.
6. Skelly, P. J. and Tighe, B. J.: Novel macroporous hydrogel adsorbents for artificial liver support perfusion systems, Polymer, 20: 1051–1052, 1979.
7. Oxley, H. R., Corkhill, P. H., Fitton, J. H., and Tighe, B. J.: Macroporous hydrogels for biomedical applications: Methodology and morphology, Biomaterials, 14: 1065–1072, 1993.
8. Barvic, M., Kliment, K., and Zavadil, M.: Biologic properties and possible uses of polymer-like sponges, J. Biomed. Mater. Res., 1: 313–323, 1967.
9. de Groot, J. H., Nijenhuis, A. J., Bruin, P., Pennings, A. J., Veth, R. P. H., Klompmaker, J., and Jansen, H. W. B.: Use of porous biodegradable polymer implants in meniscus reconstruction. 1) Preparation of porous biodegradable polyurethanes for the reconstruction of meniscus lesions, Colloid and Polymer Science, 268: 1073–1081, 1990.
10. Park, H. and Park, K.: Hydrogel foams: A new type of fast swelling hydrogels, The 20th Annual Meeting of the Society for Biomaterials, Abstract #158, 1994A.
11. Park, H. and Park, K.: Honey, I blew up the hydrogels!, Proc. Intern. Symp. Control. Rel. Bioact. Mater., 21: 21–22, 1994B.
12. Kon, M. and de Visser, A. C.: A poly(HEMA) sponge for restoration of articular cartilage defects., Plast. Reconstruct. Surg., 67: 288–294, 1981.
13. Krauch, C. H. and Sanner, A.: Polymerization on a crystalline matrix. (in German), Natur. Wissenscheften, 55: 539–540, 1968.
14. Badiger, M. V., McNeill, M. E., and Graham, N. B.: Porogens in the preparation of microporous hydrogels based on poly(ethylene oxides), Biomaterials, 14: 1059–1063, 1993.
15. Haldon, R. A. and Lee, B. E.: Structure and permeability of porous films of poly(hydroxy ethyl methacrylate), Br. Polym. J., 4: 491–501, 1972.
16. Loree, H. M., Yannas, I. V., Mikic, B., Chang, A. S., Perutz, S. M., Norregaard, T. V., and Karup, C.: Freeze-drying process for fabrication of polymeric bridges for peripheral nerve regeneration., Fifteenth Annual Northeast Bioengineering Conference, 53–54, 1989.
17. Cole, S. M., Garbe, J. E., and Woodson, L. P.: Water-insoluble polysaccharie hydrogel foam for medical applications, U.S. Pat. No. 5,089,606, 1992.
18. Gross, J. R.: Process for forming a porous particle of an absorbent polymer, U.S. Pat. No. 5,403,870, 1995.
19. Dusek, K. and Sedlacek, B.: Structure and properties of hydrophilic polymers and their gels. XI. Microsyneresis in swollen poly(ethylene glycol methacrylate) gels induced by changes in temperature, Coll. Czech. Chem. Commun., 34: 136–157, 1969.

20. Young, A. T.: Microcellular foams via phase separation, *J. Vac. Sci. Technol.,* A4: 1126–1133, 1985.
21. Kabra, B. G. and Gehrke, S. H.: Synthesis of fast response, temperature-sensitive poly(N-isopropylacrylamide) gel, *Polymer Communications,* 32: 322–323, 1991.
22. Yan, Q. and Hoffman, A. S.: Synthesis of macroporous hydrogels with rapid swelling and deswelling properties for delivery of macromolecules, *Polymer Communications,* 36: 887–889, 1995.
23. Wu, X. S., Hoffman, A. S., and Yager, P.: Synthesis and characterization of thermally reversible macroporous poly (N-isopropylacrylamide) hydrogels, *Journal of Polymer Science: Part A: Polymer Chemistry,* 30: 2121–2129, 1992.
24. Kabra, B. G. and Gehrke, S. H.: Rate-limiting steps for solvent sorption and desorption by microporous stimuli-sensitive absorbent gels, in *Superabsorbent Polymers,* American Chemical Society, Washington, D.C., 1994, 76–86.
25. Rezai, E., Lahrman, F. H., and Iwasaki, T.: Porous, absorbent macrostructures of bonded absorbent particles surface crosslinked with cationic amino-epichlorohydrin adducts, U.S. Pat. No. 5,324,561, 1994.
26. Hartley, F. D., Cross, M. M., and Lord, F. W.: The mechanism of polyurethane foam formation, in *Advances in Polyurethane Technology,* John Wiley and Sons Inc., New York, N.Y., 1968, 139.
27. Klempner, D. and Frisch, K. C. *Polymeric Foams,* Hanser Publishers, New York, 1991, Pages.
28. Gordon, A. H. *Electrophoresis of proteins in polyacrylamide and starch gels,* American Elsevier Publishing Company, Inc., New York, N.Y., 1971, Pages.
29. Arshady, R.: Albumin microspheres and microcapsules: methodology of manufacturing techniques, *Journal of Controlled Release,* 14: 111–131, 1990.
30. Tanaka, T. and Fillmore, D. J.: Kinetics of swelling of gels, *J. Chem. Phys.,* 70: 1214–1218, 1979.
31. Gehrke, S. H.: Synthesis, ewuilibrium swelling, kinetics permeability and applications of environmentally responsive gels, in *Responsive Gels: Volume Transitions II,* Springer-Verlag, New York, 1993, 81–144.
32. Knack, I. and Beckert, W.: Superabsorbent fibre flocks, methods for their production and application, U.S. Pat. No. 5,002,814 (1991).
33. Takeda, H. and Taniguchi, Y.: Production process for highly water absorbable polymer, U.S. Pat. No. 4,525,527 (1985).
34. Shutov, F. A.: Cellular structure and properties of foamed polymers, in *Polymeric Foams,* Hanser Publishers, New York, 1991, 34–35.
35. Kellenberger, S. R., Shih-Schroeder, W.-H., and Wisneski, A. J.: Absorbent structure, U.S. Pat. No. 5,149,335 (1992).
36. Holly, F. J. and Refojo, M. F.: Water wettability of hydrogels, in *Hydrogels for Medical and Related Applications,* American Chemical Society, Washington D.C., 1976, 252–266.
37. Ratner, B. D.: Hydrogel surfaces, in *Hydrogels in Medicine and Pharmacy. Volume I. Fundamentals,* CRC Press, Inc., Boca Raton, Fla., 1986, 85–94.
38. Kanig, J. L. and Rudnic, E. M.: The mechanisms of disintegrant action, *Pharmaceutical Technology,* April: 50–63, 1984.
39. Gissinger, D. and Stamm, A.: A comparative evaluation of the properties of some tablet disintegrants, *Drug Development and Industrial Pharmacy,* 6: 511–536, 1980.
40. DesMarais, T. A. and Stone, K. J.: Method for hydrophilizing absorbent foam materials using sorbitan monolaurate, U.S. Pat. No. 5,292,777, 1994.
41. Anderson, D. M. and Ström, P.: Polymerized lyotropic liquid crystals as contact lens materials, *Physica A,* 176: 151–167, 1991.

What is claimed is:

1. A hydrogel composite comprising an interpenetrating network of a crosslinked polymer and particles of a disintegrant, wherein:
    said crosslinked polymer is formed from at least one ethylenically-unsaturated monomer and a multi-olefinic crosslinking agent; and
    said disintegrant is at least one of (i) a crosslinked natural or synthetic polyelectrolyte, (ii) a crosslinked neutral hydrophilic polymer, (iii) a non-crosslinked natural or synthetic polyelectrolyte having a particulate shape, (iv) a non-crosslinked neutral hydrophilic polymer having a particulate shape, or (v) a porous inorganic material that provides wicking by capillary forces.

2. The hydrogel composite of claim 1, wherein the ratio of disintegrant to polymer is in the range of 1:100 to 100:100.

3. The hydrogel composite of claim 1, wherein the ratio of multi-olefinic crosslinking agent to monomer is in the range of 0.01:100 to 10:100.

4. The hydrogel composite of claim 1, wherein the at least one ethylenically-unsaturated monomer is selected from the group consisting of (meth)acrylic acid, salts of (meth)acrylic acid, esters of (meth)acrylic acid, salts and acids of esters of (meth)acrylic acid, amides of (meth)acrylic acid, N-alkyl amides of (meth)acrylic acid, salts and acids of N-alkyl amides of (meth)acrylic acid, N-vinyl pyrrolidinone, acrylamide, acrylamide derivatives, methacrylamide, methacrylamide derivatives, and mixtures thereof.

5. The hydrogel composite of claim 1, wherein the at least one ethylenically-unsaturated monomer is selected from the group consisting of acrylamide (AM), N-isopropylacrylamide (NIPAM), 2-hydroxyethyl methacrylate (HEMA), 2-hydroxypropyl methacrylate (HPMA), N-vinyl pyrrolidinone (VP), acrylic acid (AA), 2-acrylamido-2-methyl-1-propanesulfonic acid (AMPS), 3-sulfopropyl acrylate potassium salt (SPAK), 2-(acryloyloxy)ethyltrimethyl-ammonium methyl sulfate (ATMS), inorganic salts thereof, and mixtures thereof.

6. The hydrogel composite of claim 1, wherein the crosslinking agent is selected from the group consisting of N,N'-methylenebisacrylamide, ethylene glycol di(meth)acrylate, piperazine diacrylamide, glutaraldehyde, epichlorohydrin, crosslinking agents containing 1,2-diol structures, crosslinking agents containing functionalized peptides, and crosslinking agents containing proteins.

7. The hydrogel composite of claim 1, wherein the particles of disintegrant are selected from the group consisting of crosslinked sodium carboxymethylcellulose, crosslinked sodium starch glycolate, crosslinked sodium carboxymethyl starch, crosslinked dextran sulfate, crosslinked chitosan, crosslinked hyaluronic acid, crosslinked sodium alginate, crosslinked pectinic acid, crosslinked deoxyribonucleic acids, crosslinked ribonucleic acid, crosslinked gelatin, crosslinked albumin, polyacrolein potassium, sodium glycine carbonate, crosslinked poly(acrylic acid), crosslinked poly(styrene sulfonate), crosslinked poly(aspartic acid), crosslinked polylysine, crosslinked polyvinylpyrrolidone, crosslinked ultramylopectin, crosslinked poly(ethylene glycol), crosslinked neutral cellulose derivatives, microcrystalline cellulose, powdered cellulose, cellulose fiber, and crosslinked starch.

8. The hydrogel composite of claim 1, which has a swelling ratio in the range of 2 to 1,000.

9. The hydrogel composite of claim 1, which has a compression modulus in the range of 0.01 to 5 kg/cm$^2$.

10. The hydrogel composite of claim 1, which has a swelling time in the range of 10 seconds to 10 hours for a sample having a size in the range of 0.01 cm$^3$ and larger.

11. A superporous hydrogel composite having a superporous pore structure comprising an interpenetrating network of a crosslinked polymer and particles of a disintegrant, wherein:

said crosslinked polymer is formed from at least one ethylenically-unsaturated monomer and a multi-olefinic crosslinking agent; and said disintegrant is at least one of (i) a crosslinked natural or synthetic polyelectrolyte, (ii) a crosslinked neutral hydrophilic polymer, (iii) a non-crosslinked natural or synthetic polyelectrolyte having a particulate shape, (iv) a non-crosslinked neutral hydrophilic polymer having a particulate shape, or (v) a porous inorganic material that provides wicking by capillary forces.

12. The superporous hydrogel composite of claim 11, wherein the ratio of disintegrant to polymer is in the range of 1:100 to 100:100.

13. The superporous hydrogel composite of claim 11, wherein the ratio of multi-olefinic crosslinking agent to monomer is in the range of 0.01:100 to 10:100.

14. The superporous hydrogel composite of claim 11, wherein the at least one ethylenically-unsaturated monomer is selected from the group consisting of (meth)acrylic acid, salts of (meth)acrylic acid, esters of (meth)acrylic acid, salts and acids of esters of (meth)acrylic acid, amides of (meth) acrylic acid, N-alkyl amides of (meth)acrylic acid, salts and acids of N-alkyl amides of (meth)acrylic acid, N-vinyl pyrrolidinone, acrylamide, acrylamide derivatives, methacrylamide, methacrylamide derivatives, and mixtures thereof.

15. The superporous hydrogel composite of claim 11, wherein the at least one ethylenically-unsaturated monomer is selected from the group consisting of acrylamide (AM), N-isopropylacrylamide (NIPAM), 2-hydroxyethyl methacrylate (HEMA), 2-hydroxypropyl methacrylate (HPMA), N-vinyl pyrrolidinone (VP), acrylic acid (AA), 2-acrylamido-2-methyl-1-propanesulfonic acid (AMPS), 3-sulfopropyl acrylate potassium salt (SPAK), 2-(acryloyloxy)ethyltrimethyl-ammonium methyl sulfate (ATMS), inorganic salts thereof, and mixtures thereof.

16. The superporous hydrogel composite of claim 11, wherein the crosslinking agent is selected from the group consisting of N,N'-methylene-bisacrylamide, ethylene glycol di(meth)acrylate, piperazine diacrylamide, glutaraldehyde, epichlorohydrin, crosslinking agents containing 1,2-diol structures, crosslinking agents containing functionalized peptides, and crosslinking agents containing proteins.

17. The superporous hydrogel composite of claim 11, wherein the particles of disintegrant are selected from the group consisting of crosslinked sodium carboxymethylcellulose, crosslinked sodium starch glycolate, crosslinked sodium carboxymethyl starch, crosslinked dextran sulfate, crosslinked chitosan, crosslinked hyaluronic acid, crosslinked sodium alginate, crosslinked pectinic acid, crosslinked deoxyribonucleic acids, crosslinked ribonucleic acid, crosslinked gelatin, crosslinked albumin, polyacrolein potassium, sodium glycine carbonate, crosslinked poly(acrylic acid), crosslinked poly(styrene sulfonate), crosslinked poly(aspartic acid), crosslinked polylysine, crosslinked polyvinylpyrrolidone, crosslinked ultramylopectin, crosslinked poly(ethylene glycol), crosslinked neutral cellulose derivatives, microcrystalline cellulose, powdered cellulose, cellulose fiber, and crosslinked starch.

18. The superporous hydrogel composite of claim 11, which has a swelling ratio in the range of 5 to 5000.

19. The superporous hydrogel composite of claim 11, which has a swelling time in the range of 1 second to 1 hour for a sample having a size in the range of 0.01 cm$^3$ and larger.

20. A superporous hydrogel composite comprising an interpenetrating network of a crosslinked polymer and particles of a disintegrant, said composite prepared by a process comprising:

combining at least one ethylenically-unsaturated monomer, a multi-olefinic crosslinking agent, particles of a disintegrant, and a blowing agent to form an admixture thereof; and subjecting said admixture to polymerization and foaming conditions to form said superporous hydrogel composite, wherein said disintegrant is at least one of (i) a crosslinked natural or synthetic polyelectrolyte, (ii) a crosslinked neutral hydrophilic polymer, (iii) a non-crosslinked natural or synthetic polyelectrolyte having a particulate shape, (iv) a non-crosslinked neutral hydrophilic polymer having a particulate shape, or (v) a porous inorganic material that provides wicking by capillary forces.

21. The superporous hydrogel composite of claim 20, which has an average pore size in the range of 10 $\mu$m to 3,000 $\mu$m.

22. The superporous hydrogel composite of claim 20, which has an average pore size in the range of 50 $\mu$m to 1,000 $\mu$m.

23. The superporous hydrogel composite of claim 20, which has an average pore size in the range of 100 $\mu$m to 600 $\mu$m.

24. The superporous hydrogel composite of claim 20, wherein the ratio of disintegrant to polymer is in the range of 1:100 to 100:100.

25. The superporous hydrogel composite of claim 20, wherein the ratio of crosslinking agent to monomer is in the range of 0.01:100 to 10:100.

26. The superporous hydrogel composite of claim 20, wherein the blowing agent is $NaHCO_3$, $Na_2CO_3$, $CaCO_3$, or gas bubbles introduced from an external source.

27. The superporous hydrogel composite of claim 20, wherein the swelling ratio is in the range of 5 to 5,000.

28. The superporous hydrogel composite of claim 20, wherein the swelling time is in the range of 1 second to 1 hour.

29. The superporous hydrogel composite produced by drying the composite formed in claim 20 by air-drying or by replacing water in the composite with an organic solvent followed by air drying.

30. The superporous hydrogel composite of claim 29, which upon drying exhibits elastic properties of compression, extension, and folding without breaking.

31. The superporous hydrogel composite produced by drying the superporous hydrogel composite formed in claim 20 by freeze-drying after partial swelling or equilibrium swelling in aqueous solution.

32. The superporous hydrogel composite of claim 31, which upon drying exhibits elastic properties of compression, extension, and folding without breaking.

33. A method of forming a hydrogel composite comprising:
- combining at least one ethylenically-unsaturated monomer, a multi-olefinic crosslinking agent, and particles of a disintegrant, to form an admixture thereof; and
- subjecting the admixture to polymerization conditions to form said hydrogel composite.

34. The method of claim 33, further combining water with said admixture prior to subjecting the admixture to said polymerization conditions.

35. The method of claim 33, further combining a polymerization initiator with said admixture prior to subjecting the admixture to said polymerization conditions.

36. A method of forming a superporous hydrogel composite comprising:
- combining at least one ethylenically-unsaturated monomer, a multi-olefinic crosslinking agent, particles of a disintegrant, and a blowing agent, to form an admixture thereof; and
- subjecting the admixture to polymerization and foaming conditions to form said superporous hydrogel composite.

37. The method of claim 36, wherein said at least one ethylenically-unsaturated monomer, multi-olefinic crosslinking agent, and particles of a disintegrant are combined prior to combining the blowing agent therewith.

38. The method of claim 36, further combining water with said admixture prior to subjecting the admixture to said polymerization and foaming conditions.

39. The method of claim 36, further combining a foam stabilizing agent with said admixture prior to subjecting the admixture to said polymerization and foaming conditions.

40. The method of claim 36, further combining a polymerization initiator with said admixture prior to subjecting the admixture to said polymerization and foaming conditions.

* * * * *